United States Patent
Grosse-Sender et al.

(10) Patent No.: US 12,012,420 B2
(45) Date of Patent: Jun. 18, 2024

(54) SOLID FORMS OF [(1S)-1-[(2S,4R,5R)-5-(5-AMINO-2-OXO-THIAZOLO[4,5-D]PYRIMIDIN-3-YL)-4-HYDROXY-TETRAHYDROFURAN-2-YL]PROPYL] ACETATE

(71) Applicant: Hoffmann-La Roche Inc., Little Falls, NJ (US)

(72) Inventors: Katja Grosse-Sender, Basel (CH); Urs Schwitter, Basel (CH); Frank Stowasser, Basel (CH); Xuemei Wang, Shanghai (CN); Jing Xiong, Shanghai (CN)

(73) Assignee: Hoffmann-La Roche, Inc., Little Falls, NJ (US)

( * ) Notice: Subject to any disclaimer, the term of this patent is extended or adjusted under 35 U.S.C. 154(b) by 0 days.

(21) Appl. No.: 17/645,875

(22) Filed: Dec. 23, 2021

(65) Prior Publication Data

US 2022/0119414 A1    Apr. 21, 2022

Related U.S. Application Data

(63) Continuation of application No. 16/476,172, filed as application No. PCT/EP2018/050160 on Jan. 4, 2018, now Pat. No. 11,230,559.

(30) Foreign Application Priority Data

Nov. 21, 2017   (WO) ................ PCT/CN2017/112151

(51) Int. Cl.
   C07D 513/04    (2006.01)
   A61P 31/20     (2006.01)

(52) U.S. Cl.
   CPC ............ C07D 513/04 (2013.01); A61P 31/20 (2018.01); *C07B 2200/13* (2013.01)

(58) Field of Classification Search
   CPC .................................................. C07D 513/04
   USPC ...................................................... 514/260.1
   See application file for complete search history.

(56) References Cited

U.S. PATENT DOCUMENTS

| | | | |
|---|---|---|---|
| 9,441,008 B2 | 9/2016 | Chen et al. | |
| 11,230,559 B2 * | 1/2022 | Grosse-Sender | ....... A61P 31/12 |
| 2018/0000824 A1 | 1/2018 | Dai et al. | |
| 2022/0119415 A1 | 4/2022 | Grosse-Sender et al. | |

FOREIGN PATENT DOCUMENTS

| | | |
|---|---|---|
| CN | 103476770 A | 12/2013 |
| JP | 2010-526129 A | 7/2010 |
| WO | 2016/091698 A1 | 6/2016 |
| WO | 2016/146598 A1 | 9/2016 |
| WO | 2016/176665 A1 | 11/2016 |
| WO | 2017/211791 A1 | 12/2017 |
| WO | 2018/127525 A1 | 7/2018 |

OTHER PUBLICATIONS

Balbach et al., "Pharmaceutical evaluation of early development candidates the 100 mg-approach" International Journal of Pharmaceutics. 275:1-12 ( 2004).
Caira, M.R., Design of Organic Solids "Crystalline Polymorphism of Organic Compounds" Weber, E, Aoyama, Y, et al, eds., Berlin, Heidelberg-Germany:Springer, vol. 198:163-208 ( 1998).
International Preliminary Report on Patentability (IPRP for PCT/EP2018/050160 issued on Jul. 9, 2019.
International Search Report for PCT/EP2018/050160 mailed on Sep. 18, 2018.
Matsuda, Y., et al., "Pharmaceutical engineering problems related to polymorphism" J Society Powder Technol-JP 21(11):704-714 (Nov. 10, 1984).
Mirmehrabi et al., "An Approach to Solvent Screening for Crystallization of Polymorphic Pharmaceuticals and Fine Chemicals" Journal of Pharmaceutical Sciences 94:1560-1576 ( 2005).
Singhal et al., "Drug polymorphism and dosage form design: a practical perspective" Advanced Drug Delivery Reviews 56:335-347 ( 2004).

* cited by examiner

*Primary Examiner* — Kahsay Habte
(74) *Attorney, Agent, or Firm* — Genentech, Inc.; Richard G. A. Bone

(57) ABSTRACT

The present invention relates to novel solid forms of compound (I),

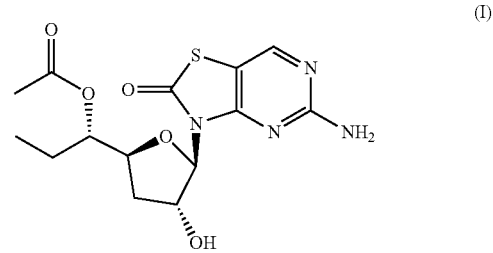

(I)

[(1S)-1-[(2S,4R,5R)-5-(5-amino-2-oxo-thiazolo[4,5-d]pyrimidin-3-yl)-4-hydroxy-tetrahydrofuran-2-yl]propyl] acetate and pharmaceutical compositions comprising the solid forms thereof disclosed herein, which may be used as a TLR7 agonist, or for the treatment or prophylaxis of a viral disease in a patient relating to HBV infection or a disease caused by HBV infection.

16 Claims, 19 Drawing Sheets

SOLID FORMS OF [(1S)-1-[(2S,4R,5R)-5-(5-AMINO-2-OXO-THIAZOLO[4,5-D]PYRIMIDIN-3-YL)-4-HYDROXY-TETRAHYDROFURAN-2-YL]PROPYL] ACETATE

CLAIM OF PRIORITY

This application claims the benefit of priority under 35 U.S.C. § 120 to, and is a continuation of, U.S. patent application Ser. No. 16/476,172, filed Jul. 5, 2019, which is the U.S. national stage under 35 U.S.C. § 371 of International Application Number PCT/EP2018/050160, having an international filing date of Jan. 4, 2018, which claims benefit of priority to China Patent Application Number PCT/CN2017/112151, filed Nov. 21, 2017, all of which are incorporated herein by reference in their entirety.

TECHNICAL FIELD

The present invention relates to novel solid forms of compound (I),

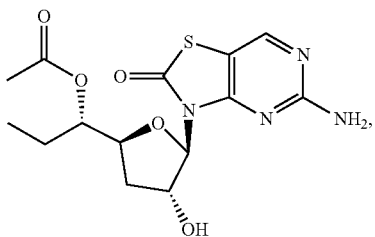

(I)

[(1S)-1-[(2S,4R,5R)-5-(5-amino-2-oxo-thiazolo[4,5-d]pyrimidin-3-yl)-4-hydroxy-tetrahydrofuran-2-yl]propyl]acetate, and pharmaceutical compositions comprising solid forms thereof disclosed herein, which may be used as a TLR7 agonist, or for the treatment or prophylaxis of a viral disease in a patient relating to HBV infection or a disease caused by HBV infection.

BACKGROUND

The current therapy of chronic HBV infection is based on two different types of drugs: the traditional antiviral nucleoside/nucleotide analogues and the more recent Pegylated IFN-α (PEG-IFN-α). The oral nucleoside/nucleotide analogues act by suppressing the HBV replication. This is a life-long course of treatment during which drug resistance often occurs. As an alternative option, Pegylated IFN-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated IFN-α (PEG-IFN-α) is currently used to treat chronic HBV and is an alternative to potentially life-long treatment with antiviral nucleoside/nucleotide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleoside/nucleotide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability.

[(1S)-1-[(2S,4R,5R)-5-(5-amino-2-oxo-thiazolo[4,5-d]pyrimidin-3-yl)-4-hydroxy-tetrahydrofuran-2-yl]propyl]acetate (compound (I)) was disclosed in WO2016091698 as an effective TLR7 agonist.

It was found that Form Amorphous of compound (I) was prone to crystallization which leads to form change and makes it not suitable for further drug development. As one of the objectives of this patent, several novel solid forms were identified and characterized, showing significantly improved stability compared with Form Amorphous of compound (I). Meanwhile, developing novel crystalline forms of compound (I) with good processability or acceptable aqueous solubility is also one of the objectives of current invention. Some novel solid forms enhanced the developability of compound (I) fundamentally.

The present disclosure relates generally to the novel solid forms of compound (I) and processes to make them.

In another embodiment, Form C of compound (I) shows significantly improved stability and comparable apparent solubility compared with Form Amorphous of compound (I) and/or other solid forms. The physical stability of drug substances is an integral part of the systematic approach to the stability evaluation of pharmaceuticals due to its potential impacts on drug chemical stability performance and safety. The greater the stability is, the longer the shelf life could be. Therefore the accelerated and long term stability testing used in this invention could be used to predict shelf lives. Furthermore, solubility is one of the important parameters to achieve desired concentration of drug in systemic circulation for desired pharmacological response. Generally speaking, amorphous pharmaceuticals are markedly more soluble than their crystalline counterparts. Surprisingly, Form C of compound (I) shows comparable apparent solubility compared with Form Amorphous of compound (I) and ensures the in vivo absorption. The unexpected property improvement of Form C makes it more suitable for further drug development.

In another embodiment, Form D of compound (I) is an ethyl acetate solvate.

In another embodiment, Form E of compound (I) is a process related form which exhibits excellent impurity purification effect.

The bioavailability of many drugs can be dependent on polymorphs that show different solubility and absorption rate. Moreover, in vivo conversion of the prodrug to active form was confirmed to be polymorph-dependent. Compound (I) is a double prodrug, the conversion from double prodrug to single prodrug and active form can be dependent on the solid forms of this invention. The SDPK study was performed on Form A and C to demonstrate such effect. As the result, Form A of compound (I) exhibits faster conversion rate (shorter $T_{max}$ and higher $C_{max}$) to the single prodrug and high $C_{max}$ of active form in vivo study, and therefore Form A of compound (I) is more preferred with immediate-release oral formulation.

In another embodiment, Form B of compound (I) is more preferred with oral suspension formulation. Conversion of Form Amorphous of compound (I) or Form A of compound (I) to Form B of compound (I) in aqueous compositions was observed. Therefore, Form B of compound (I) shows better stability in aqueous environment.

In another embodiment, Form G of compound (I) shows improved stability and comparable apparent solubility compared with Form Amorphous of compound (I). With regard to general solid formulation development, the melting point of a synthetic substance should not be below 80° C. (Stefan Balbach, 2004, Pharmaceutical evaluation of early development candidates "the 100 mg-approach", International Journal of Pharmaceutics 275 (2004) 1-12). Form C, F and G of compound (I) with the onset melting point at 128.9° C., 141.2° C. and 122.0° C. respectively are therefore much more preferred with respect to solid formulation development compared to the other forms of this invention.

SUMMARY

The present invention relates to polymorphs, salts, solvates, co-crystals or combinations thereof and methods for the synthesis and production of solid forms of [(1S)-1-[(2S, 4R,5R)-5-(5-amino-2-oxo-thiazolo[4,5-d]pyrimidin-3-yl)-4-hydroxy-tetrahydrofuran-2-yl]propyl]acetate.

In one embodiment, provided herein is an amorphous or solid form of compound (I) or solvates or combination thereof.

In another embodiment, provided herein is an amorphous or solid form of compound (I), wherein the solid form is Form A, Form B, Form C, Form D, Form E, Form F, Form G, Form H, Form I or Form J, or a combination thereof.

In another embodiment, the solid form of compound (I) is Form C that exhibits an X-ray powder diffraction (XRPD) pattern with characteristic peaks expressed in degrees 2-theta at 6.0°±0.2°, 11.3°±0.2°, 15.4°±0.2°, 16.2°±0.2°, 20.0°±0.2°, 21.4°±0.2°, 24.6°±0.2° and 26.1°±0.2°.

In a further embodiment, the solid form of compound (I) is Form C that exhibits an X-ray powder diffraction (XRPD) pattern with characteristic peaks expressed in degrees 2-theta at 6.0°±0.2°, 11.3°±0.2°, 13.2°±0.2°, 15.4°±0.2°, 16.2°±0.2°, 18.1°±0.2°, 19.3°±0.2°, 20.0°±0.2°, 21.4°±0.2°, 23.5°±0.2°, 24.6°±0.2°, 25.6°±0.2°, 26.1°±0.2° and 32.5°±0.2°.

In a further embodiment, the solid form of compound (I) is Form C that exhibits an X-ray powder diffraction (XRPD) pattern shown in FIG. 3

In a further embodiment, the solid form of compound (I) is Form C with a differential scanning calorimetry (DSC) thermogram comprising endothermic peak with onset temperature at 128.9° C.±3° C.

In another embodiment, the solid form of compound (I) is Form D that exhibits an X-ray powder diffraction (XRPD) pattern with characteristic peaks expressed in degrees 2-theta at 6.6°±0.2°, 17.5°±0.2°, 20.5°±0.2°, 20.8°±0.2°, 26.1°±0.2° and 28.7°±0.2°.

In a further embodiment, the solid form of compound (I) is Form D that exhibits an X-ray powder diffraction (XRPD) pattern with characteristic peaks expressed in degrees 2-theta at 6.6°±0.2°, 10.9°±0.2°, 11.2°±0.2°, 15.3°±0.2°, 17.1°±0.2°, 17.5°±0.2°, 19.0°±0.2°, 20.5°±0.2°, 20.8°±0.2°, 22.1°±0.2°, 24.2°±0.2°, 25.4°±0.2°, 26.1°±0.2°, 28.7°±0.2° and 33.3°±0.2°.

In a further embodiment, the solid form of compound (I) is Form D that exhibits an X-ray powder diffraction (XRPD) pattern shown in FIG. 6.

In a further embodiment, the solid Form D is an ethyl acetate solvate of compound (I).

In a further embodiment, the solid form is Form D with the X-ray crystal structure showed in FIG. 7.

In a further embodiment, Form D is an ethyl acetate solvate of compound (I).

In another embodiment, the solid form of compound (I) is Form E that exhibits an X-ray powder diffraction (XRPD) pattern with characteristic peaks expressed in degrees 2-theta at 6.4°±0.2°, 7.4°±0.2°, 7.6°±0.2°, 9.0°±0.2°, 13.4°±0.2°, 16.2°±0.2° and 21.7°±0.2°.

In a further embodiment, the solid form of compound (I) is Form E that exhibits an X-ray powder diffraction (XRPD) pattern with characteristic peaks expressed in degrees 2-theta at 6.4°±0.2°, 7.4°±0.2°, 7.6°±0.2°, 9.0°±0.2°, 9.7°±0.2°, 13.4°±0.2°, 14.4°±0.2°, 15.7°±0.2°, 16.2°±0.2°, 18.2°±0.2°, 21.0°±0.2°, 21.3°±0.2°, 21.7°±0.2°, 23.5°±0.2° and 25.5°±0.2°.

In a further embodiment, the solid form of compound (I) is Form E that exhibits an X-ray powder diffraction (XRPD) pattern shown in FIG. 2.

In another embodiment, the solid form of compound (I) is Form A that exhibits an X-ray powder diffraction (XRPD) pattern with characteristic peaks expressed in degrees 2-theta at 3.7°±0.2°, 6.5°±0.2°, 7.5°±0.2°, 12.6°±0.2°, 15.2°±0.2°, 16.4°±0.2°, 22.4°±0.2°, 22.7°±0.2° and 23.4°±0.2°.

In a further embodiment, the solid form of compound (I) is Form A that exhibits an X-ray powder diffraction (XRPD) pattern with characteristic peaks expressed in degrees 2-theta at 3.7°±0.2°, 6.5°±0.2°, 7.5°±0.2°, 12.1°±0.2°, 12.6°±0.2°, 15.2°±0.2°, 16.4°±0.2°, 16.9°±0.2°, 20.8°±0.2°, 21.4°±0.2°, 22.1°±0.2°, 22.4°±0.2°, 22.7°±0.2°, 23.4°±0.2°, 24.6°±0.2°, 26.2°±0.2°, 26.2°±0.2° and 26.8°±0.2°.

In a further embodiment, the solid form of compound (I) is Form A that exhibits an X-ray powder diffraction (XRPD) pattern shown in FIG. 8.

In another embodiment, the solid form of compound (I) is Form B that exhibits an X-ray powder diffraction (XRPD) pattern with characteristic peaks expressed in degrees 2-theta at 4.9°±0.2°, 6.5°±0.2°, 8.3°±0.2°, 13.3°±0.2°, 13.6°±0.2°, 24.5°±0.2° and 25.9°±0.2°.

In a further embodiment, the solid form of compound (I) is Form B that exhibits an X-ray powder diffraction (XRPD) pattern with characteristic peaks expressed in degrees 2-theta at 4.9°±0.2°, 6.5°±0.2°, 8.3°±0.2°, 10.0°±0.2°, 10.3°±0.2°, 13.3°±0.2°, 13.6°±0.2°, 14.7°±0.2°, 18.3°±0.2°, 19.3°±0.2°, 20.6°±0.2°, 22.3°±0.2°, 23.1°±0.2°, 24.5°±0.2°, 25.3°±0.2° and 25.9°±0.2°.

In a further embodiment, the solid form of compound (I) is Form B that exhibits an X-ray powder diffraction (XRPD) pattern shown in FIG. 9.

In another embodiment, the solid form of compound (I) is Form G that exhibits an X-ray powder diffraction (XRPD) pattern with characteristic peaks expressed in degrees 2-theta at 5.9°±0.2°, 12.6°±0.2°, 15.9°±0.2°, 21.6°±0.2°, 24.5°±0.2° and 24.7°±0.2°.

In a further embodiment, the solid form of compound (I) is Form G that exhibits an X-ray powder diffraction (XRPD) pattern with characteristic peaks expressed in degrees 2-theta at 5.9°±0.2°, 9.6°±0.2°, 12.6°±0.2°, 15.9°±0.2°, 17.9°±0.2°, 19.9°±0.2°, 21.6°±0.2°, 24.5°±0.2°, 24.7°±0.2°, 26.3°±0.2°, 29.1°±0.2°, 32.7°±0.2° and 33.1°±0.2°.

In a further embodiment, the solid form of compound (I) is Form G that exhibits an X-ray powder diffraction (XRPD) pattern shown in FIG. 10.

In a further embodiment, the solid form of compound (I) is Form G with a differential scanning calorimetry (DSC) thermogram comprising endothermic peak with onset temperature at 122.0° C.±3° C.

In another embodiment, the solid form of compound (I) is Form F that exhibits an X-ray powder diffraction (XRPD) pattern with characteristic peaks expressed in degrees 2-theta at 7.4°±0.2°, 11.2°±0.2°, 16.0°±0.2°, 16.4°±0.2°, 17.2°±0.2°, 21.0° 0.2°, 25.0°±0.2° and 25.5°±0.2°.

In a further embodiment, the solid form of compound (I) is Form F that exhibits an X-ray powder diffraction (XRPD) pattern with characteristic peaks expressed in degrees 2-theta at 7.4°±0.2°, 9.8°±0.2°, 11.2°±0.2°, 15.7°±0.2°, 16.0°±0.2°, 16.4°±0.2°, 17.2°±0.2°, 18.1°±0.2°, 18.8°±0.2°, 19.2°±0.2°, 21.0°±0.2°, 21.2°±0.2°, 22.9°±0.2°, 25.0°±0.2°, 25.5°±0.2°, 25.7°±0.2° and 29.1°±0.2°.

In a further embodiment, the solid form of compound (I) is Form F that exhibits an X-ray powder diffraction (XRPD) pattern shown in FIG. 16.

In a further embodiment, the solid form of compound (I) is Form F with a differential scanning calorimetry (DSC) thermogram comprising endothermic peak with onset melting temperature at 141.2° C.±3° C.

In another embodiment, the solid form of compound (I) is Form H that exhibits an X-ray powder diffraction (XRPD) pattern with characteristic peaks expressed in degrees 2-theta at 11.4°±0.2°, 15.6°±0.2°, 17.3°±0.2°, 21.1°±0.2° and 21.9°±0.2°.

In a further embodiment, the solid form of compound (I) is Form H that exhibits an X-ray powder diffraction (XRPD) pattern with characteristic peaks expressed in degrees 2-theta at 6.7°±0.2°, 9.4°±0.2°, 11.1°±0.2°, 11.4°±0.2°, 15.6°±0.2°, 17.3°±0.2°, 17.6°±0.2°, 18.9°±0.2°, 19.5°±0.2°, 21.1°±0.2°, 21.9°±0.2°, 23.2°±0.2°, 25.8°±0.2° and 29.0°±0.2°.

In a further embodiment, the solid form of compound (I) is Form H that exhibits an X-ray powder diffraction (XRPD) pattern shown in FIG. 17.

In a further embodiment, Form H is a dimethyl carbonate solvate of compound (I).

In another embodiment, the solid form of compound (I) is Form I that exhibits an X-ray powder diffraction (XRPD) pattern with characteristic peaks expressed in degrees 2-theta at 11.1°±0.2°, 15.4°±0.2°, 17.2°±0.2°, 17.6°±0.2°, 20.9°±0.2° and 21.7°±0.2°.

In a further embodiment, the solid form of compound (I) is Form I that exhibits an X-ray powder diffraction (XRPD) pattern with characteristic peaks expressed in degrees 2-theta at 9.4°±0.2°, 11.1°±0.2°, 13.8°±0.2°, 14.2°±0.2°, 15.4°±0.2°, 17.2°±0.2°, 17.6°±0.2°, 19.2°±0.2°, 20.9°±0.2°, 21.7°±0.2°, 22.0°±0.2°, 23.0°±0.2°, 24.0°±0.2°, 25.2°±0.2° and 28.9°±0.2°.

In a further embodiment, the solid form of compound (I) is Form I that exhibits an X-ray powder diffraction (XRPD) pattern shown in FIG. 18.

In a further embodiment, Form I is a methyl ethyl ketone solvate of compound (I).

In another embodiment, the solid form of compound (I) is Form J that exhibits an X-ray powder diffraction (XRPD) pattern with characteristic peaks expressed in degrees 2-theta at 8.9°±0.2°, 11.0°±0.2°, 16.4°±0.2°, 19.8°±0.2°, 20.7°±0.2°, 23.7°±0.2° and 27.1°±0.2°.

In a further embodiment, the solid form of compound (I) is Form J that exhibits an X-ray powder diffraction (XRPD) pattern with characteristic peaks expressed in degrees 2-theta at 8.9°±0.2°, 11.0°±0.2°, 13.3°±0.2°, 15.0°±0.2°, 16.4°±0.2°, 16.9°±0.2°, 19.8°±0.2°, 20.7°±0.2°, 22.6°±0.2°, 23.7°±0.2°, 27.1°±0.2° and 33.4°±0.2°.

In a further embodiment, the solid form of compound (I) is Form J that exhibits an X-ray powder diffraction (XRPD) pattern shown in FIG. 19.

In a further embodiment, Form J is a methyl isobutyl ketone solvate of compound (I).

In another embodiment, provided herein is a pharmaceutical composition comprising the solid form disclosed herein; and a pharmaceutically acceptable carrier, excipient, diluent, adjuvant, vehicle or a combination thereof.

In another embodiment, provided herein is the use of the solid form disclosed herein or the pharmaceutical composition for the manufacture of a medicament for the treatment or prophylaxis of a viral disease in a patient.

In another embodiment, the viral disease disclosed herein is HBV infection or a disease caused by HBV infection.

In another embodiment, provided herein is a method for the treatment or prophylaxis of HBV infection or a disease caused by HBV infection, which method comprises administering a therapeutically effective amount of the solid form or the pharmaceutical composition disclosed herein.

ABBREVIATIONS $C_{max}$ Maximum concentration observed
FaSSIF Fasted State Simulated Intestinal Fluid
FeSSIF Fed State Simulated Intestinal Fluid
DSC Differential scanning calorimetry
Pos. Position
Rel. Int. Relative Intensity
SGF Simulated Gastric Fluid
TGA Thermal gravimetric analysis
$T_{max}$ Time at which the maximum concentration (Cmax) is observed
XRPD X-ray powder diffraction

EXAMPLES

The invention will be more fully understood by reference to the following examples. They should not, however, be construed as limiting the scope of the invention.

HPLC Method for Chemical Purity and Assay Test

HPLC conditions are disclosed here in Table 1.

TABLE 1

| HPLC conditions for chemical purity and assay test | |
|---|---|
| Instrument | Agilent 1260 with a DAD or VWD detector |
| Column | Waters Xbridge C8 (4.6 mm × 150 mm, 3.5 μm) or equivalent |
| Column Temperature | 30° C. |
| Flow Rate | 0.8 mL/min |
| Nominal Concentration | 0.1 mg/mL |
| Injection Volume | 8 μL |
| Mobile Phase A | 0.1% TFA in water |
| Mobile Phase B | 0.1% TFA in acetonitrile |

| | Time (min) | % A | % B |
|---|---|---|---|
| Gradient Program | 0.00 | 98 | 2 |
| | 3.00 | 98 | 2 |
| | 15.00 | 10 | 90 |
| | 20.00 | 10 | 90 |
| | 20.01 | 98 | 2 |
| | 25.00 | 98 | 2 |

| Diluent | 50:50 water:acetonitrile (v/v) |
|---|---|
| Detection | UV 230 nm |
| Retention Time | 10.6 min |

Example 1

Preparation of Form Amorphous of Compound (I)

Figure 1:
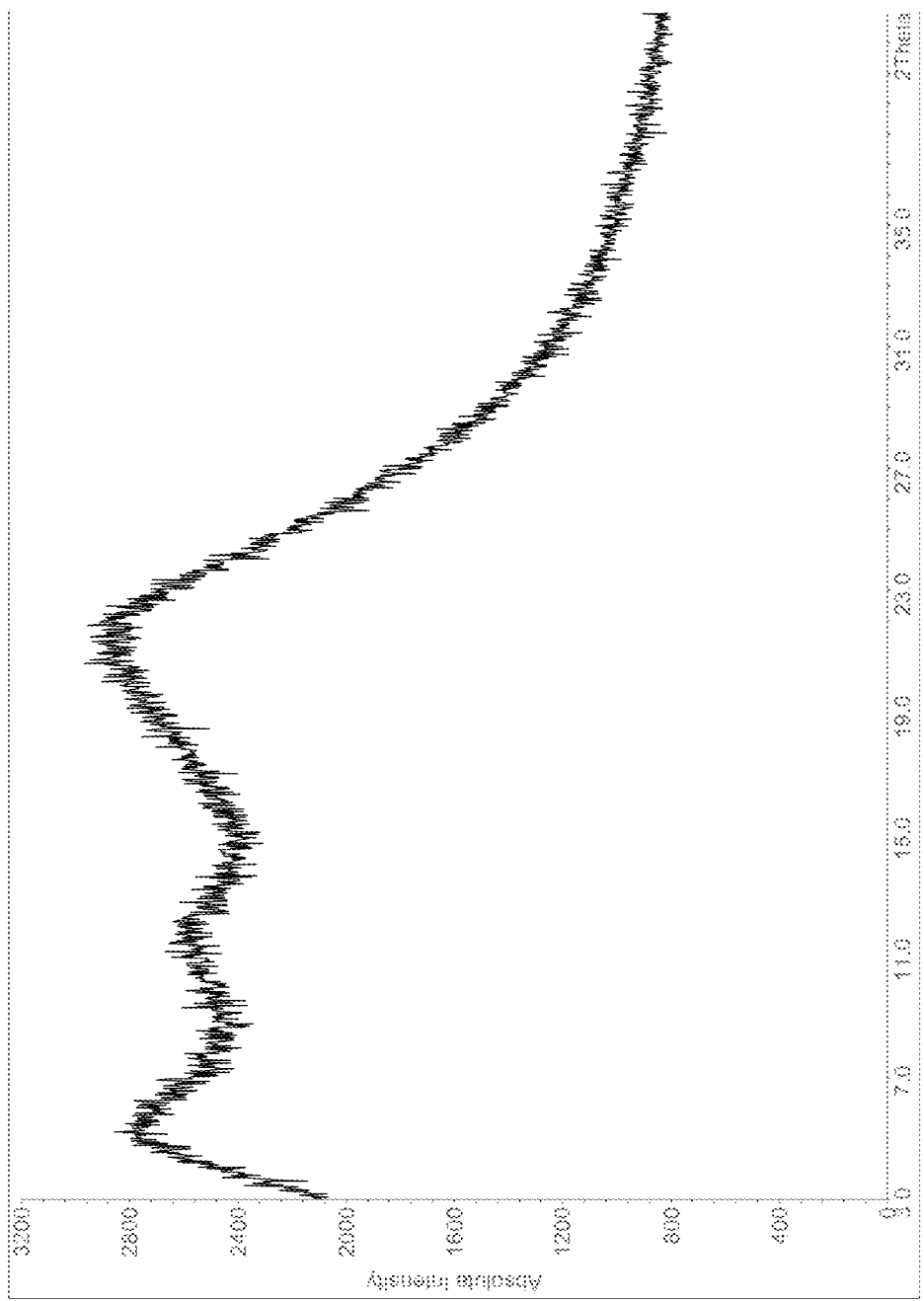
FIG. 1 X-ray powder diffraction pattern for Form Amorphous
FIG. 2 X-ray powder diffraction pattern for Form E
FIG. 3 X-ray powder diffraction pattern for Form C
FIG. 4 DSC thermogram of Form C
FIG. 5 TGA diagram of Form C
FIG. 6 X-ray powder diffraction pattern for Form D
FIG. 7 X-ray crystal structure of Form D
FIG. 8 X-ray powder diffraction pattern for Form A
FIG. 9 X-ray powder diffraction pattern for Form B
FIG. 10 X-ray powder diffraction pattern for Form G
FIG. 11 DSC thermogram of Form E
FIG. 12 DSC thermogram of Form A
FIG. 13 DSC thermogram of Form B
FIG. 14 DSC thermogram of Form G
FIG. 15 DSC thermogram of Form F
FIG. 16 X-ray powder diffraction pattern for Form F
FIG. 17 X-ray powder diffraction pattern for Form H
FIG. 18 X-ray powder diffraction pattern for Form I
FIG. 19 X-ray powder diffraction pattern for Form J

A solution of 1.0 g of compound (I) in 7 mL of acetone was rapidly evaporated using a rotary evaporator. The solid was dried under vacuum at 50° C. overnight. The solid was analyzed by XRPD. The result is shown in FIG. 1.

Characterization Method:

XRPD: X-ray diffraction patterns were recorded at ambient conditions in transmission geometry with a STOE STADI P powder diffractometer (STOE & Cie GmbH) with Cu-Kα1 radiation. The diffractometer was equipped with a primary Ge beam monochromator and a silicon strip detector. Tube voltage was 40 kV and tube current was 40 mA. Scan range was from 3 to 42 degree 2-theta. The step size was 0.02 degree 2-theta with a measurement time of 20 s per step.

Example 2

Preparation of Form E of Compound (I)

Preparation of [(1S)-1-[(2S,4R,5R)-5-(5-amino-2-oxo-thiazolo[4,5-d]pyrimidin-3-yl)-4-hydroxy-tetrahydrofuran-2-yl]propyl] Acetate Citric Acid (Compound (I))

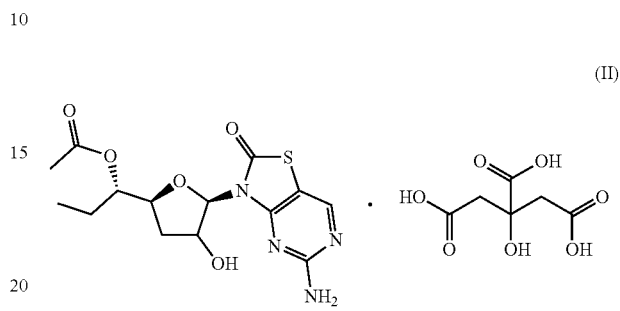

(II)

The solution of [(1S)-1-[(2S,4R,5R)-5-(5-amino-2-oxo-thiazolo[4,5-d]pyrimidin-3-yl)-4-hydroxy-tetrahydrofuran-2-yl]propyl]acetate (compound (I), 22.2 mol) in acetonitrile (69.5 kg) was heated to 45° C.-52° C. and stirred at 45° C.-52° C. for 30 minutes. To the mixture citric acid monohydrate (4.67 kg, 22.2 mol) and water (0.440 kg, $V_{water}/V_{acetonitrile}=0.005$) were charged. The resulting mixture was stirred at 45° C.-52° C. for 4 hours then cooled to 0° C. over 10 hours. The solid was separated via centrifuge and the wet cake was washed with acetonitrile (1.0 kg), and dried in a vacuum oven (30 mmHg, 40° C.) for 32 hours to afford compound (II) (9.04 kg, 74.5% yield). The ratio of compound (I) and citric acid in compound (II) was 1:1 based on NMR data.

Compound (II): $^1$H NMR (400 MHz, d$_6$-DMSO) ppm: 8.34 (s, 1H), 6.91 (br. s., 2H), 5.82 (s, 1H), 5.46-5.58 (m, 1H), 4.70-4.82 (m, 2H), 4.14-4.23 (m, 1H), 2.60-2.80 (m, 4H), 2.42-2.48 (m, 1H), 1.98 (s, 3H), 1.78-1.88 (m, 1H), 1.55-1.70 (m, 1H), 1.34-1.49 (m, 1H), 0.82 (t, J=7.40 Hz, 3H). MS obsd. (ESI$^+$) [(M+H)$^+$]: 355.

Preparation of Form E of Compound (I)

A 50 L glass jacket reactor was charged with Na$_2$CO$_3$ (0.819 kg, 7.73 mol) and water (19.8 kg). The mixture was stirred at 20° C. to 30° C. for 30 minutes and then isopropyl acetate (18.2 kg) and [(1S)-1-[(2S,4R,5R)-5-(5-amino-2-oxo-thiazolo[4,5-d]pyrimidin-3-yl)-4-hydroxy-tetrahydrofuran-2-yl]propyl]acetate citric acid (compound (II)) (3.0 kg, 5.49 mol) were added. The reaction mixture was stirred for another 3 hours at 20° C. to 30° C. After phase separation, the organic phase was washed with sat. Na$_2$CO$_3$ aq. solution (20.2 kg), water (20.0 kg), sat. NaCl aq. solution (21.7 kg). Such extraction was repeated twice. The combined organic solution was concentrated under vacuum to remove the volatile to afford a crude solution (13.04 kg), to which isopropyl acetate (6.05 kg) was then added. The reaction mixture was then heated to 40° C. to 50° C. and stirred for 1 hour, followed by slow addition of n-heptane (8.05 kg). The resulting mixture was stirred at 40° C. to 50° C. for another 12 hours. After slow cooling to 0° C. to 10° C. over 4 hours and stirred at 0° C. to 10° C. for 30 minutes, n-heptane (10.1 kg) was added and the resulting mixture was maintained at 0° C. to 10° C. for 2 hours. The suspension was separated by vacuum filtration and the wet cake was washed with n-heptane (6 kg) and dried in a vacuum oven (30 mmHg, 45° C.) for 19 hours.

Figure 2:
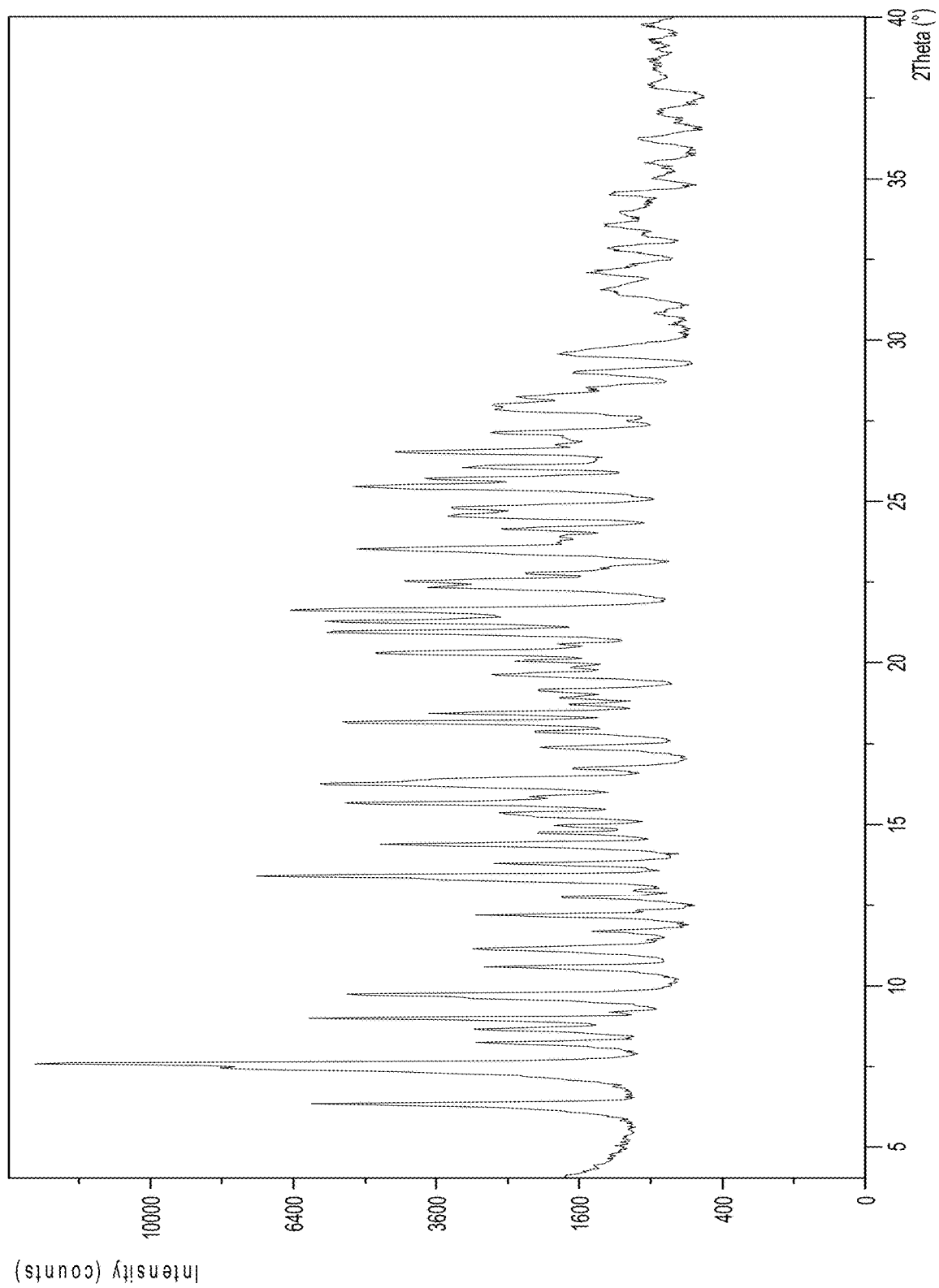

The XRPD pattern of Form E of compound (I) is shown in FIG. 2. Major peaks and their related intensities in the XRPD pattern are shown in Table 2. Depending on the solvation status Form E can be a solvate (isostructural with different solvents) or a polymorph of compound (I).

Characterization Method:

DSC analysis: TA Q2000, 30-200° C., heating rate 10° C./min.

XRPD: PANalytical EMPYREAN X-ray powder diffractometer with Cu-Kα radiation. Tube voltage was 40 kV and tube current was 40 mA. Scan range was from 4 to 40 degree 2-theta. The step size was 0.026° at a scanning speed of 3.463°/min.

TABLE 2

Powder Diffraction peaks of Form E of compound (I).

| Pos. [°2-theta] | Rel. Int. [%] |
|---|---|
| 6.4 | 41 |
| 7.4 | 56 |
| 7.6 | 100 |
| 8.2 | 15 |
| 8.7 | 16 |
| 9.0 | 41 |
| 9.7 | 37 |
| 10.6 | 17 |
| 11.2 | 19 |
| 11.7 | 6 |
| 12.2 | 19 |
| 12.7 | 10 |
| 13.4 | 53 |
| 13.8 | 16 |
| 14.4 | 31 |
| 14.7 | 11 |
| 15.0 | 8 |
| 15.4 | 15 |
| 15.7 | 37 |
| 16.2 | 42 |
| 16.4 | 23 |
| 16.7 | 8 |
| 17.4 | 11 |
| 17.9 | 11 |
| 18.2 | 37 |
| 18.4 | 22 |
| 18.7 | 6 |
| 18.9 | 6 |
| 19.2 | 8 |
| 19.6 | 13 |
| 20.1 | 10 |
| 20.3 | 30 |
| 20.6 | 6 |
| 21.0 | 38 |
| 21.3 | 38 |
| 21.7 | 46 |
| 22.3 | 23 |
| 22.6 | 27 |
| 22.8 | 11 |
| 23.5 | 34 |
| 24.2 | 13 |
| 24.5 | 20 |
| 24.8 | 20 |
| 25.5 | 34 |
| 25.7 | 23 |
| 26.1 | 17 |
| 26.5 | 28 |
| 27.1 | 15 |
| 27.8 | 14 |
| 28.0 | 15 |

Figure 11:
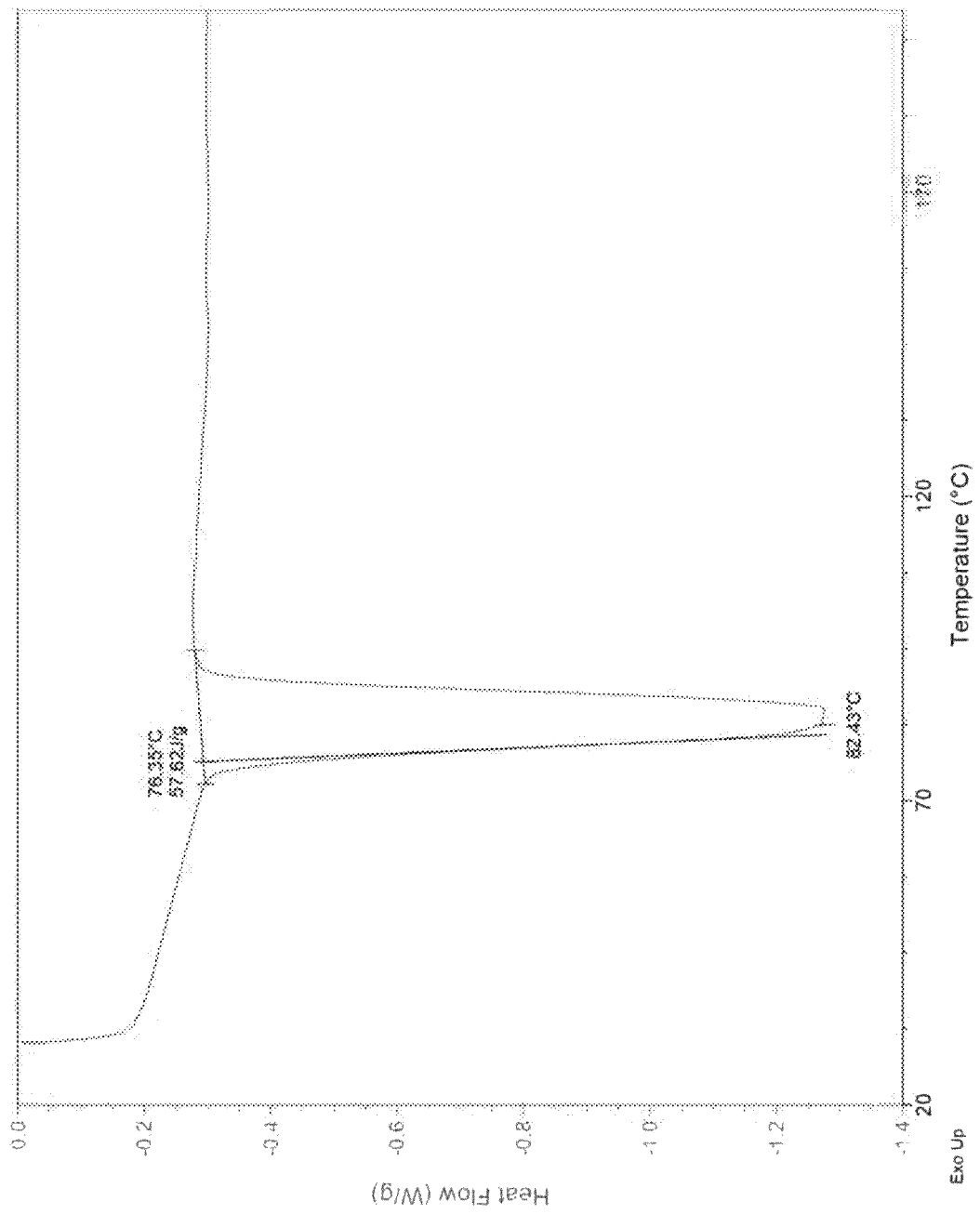

DSC result shown in FIG. 11 indicates Form E of compound (I) has an onset of endothermal event at around 76.4° C.

Example 3

Alternative Preparation of Form E of Compound (I)

Approximate 50 mg of Form Amorphous of compound (I) as prepared in Example 1 was weighed and transferred to a glass vial. 0.1 mL of isopropyl acetate was added to form a clear solution. 0.4 mL of n-heptane was added to the solution. The vial was mounted to a shaker and kept shaking at 25° C. with 1200 rpm for 4 h to generate precipitation. The solid precipitate was collected for XRPD analysis. The XRPD pattern of solid was same as that in Table 2 and confirmed to be Form E of compound (I).

Example 4

Preparation of Form C of Compound (I)

A 50 L glass jacket reactor was charged with water (35.65 kg), EtOH (3.00 kg) and 3.15 kg of Form E of compound (I) as prepared in Example 2. The mixture was heated to 40° C. to 50° C. and stirred for 19 hours. Then, after cooling to 0° C. to 10° C. over 4 hours, a suspension formed and was separated via vacuum filtration. The wet cake was washed with water (5.00 kg) twice and then dried in a vacuum oven (30 mmHg, 50° C.) for 24 hours. The solid was collected for XRPD analysis, DSC analysis, and TGA analysis.

Figure 3:
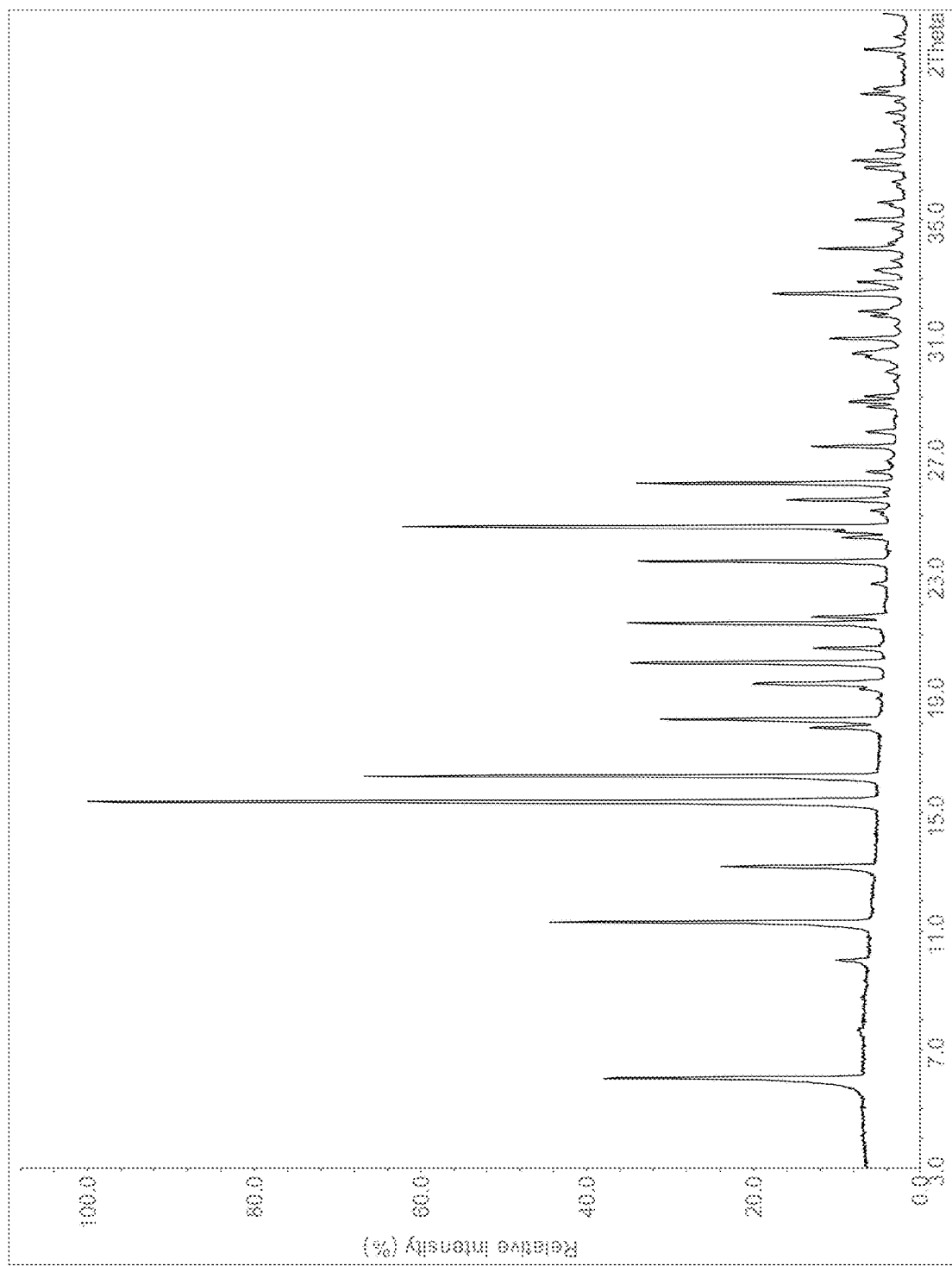

The XRPD pattern of Form C of compound (I) is shown in FIG. 3. Major peaks and their related intensities in the XRPD pattern are shown in Table 3. Form C is a polymorph of compound (I).

Characterization Methods:

XRPD: X-ray diffraction patterns were recorded at ambient conditions in transmission geometry with a STOE STADI P diffractometer with Cu-Kα1 radiation. The diffractometer was equipped with a primary Ge beam monochromator and a silicon strip detector. Tube voltage was 40 KV and tube current was 40 mA. Scan range was from 3 to 42 degree 2-theta. The step size was 0.02 degree 2-theta with a measurement time of 20 s per step. The samples were prepared and analyzed without further processing (e.g. grinding or sieving) of the substance.

DSC analysis: Mettler Toledo DSC1, 25-180° C., heating rate 10° C./min.

TGA analysis: Mettler Toledo TGA/DSC1, 25-350° C., heating rate 5° C./min.

TABLE 3

X-Ray powder diffraction peaks of Form C of compound (I).

| Pos. [°2-theta] | Rel. Int. [%] |
|---|---|
| 6.0 | 37 |
| 10.0 | 10 |
| 11.3 | 43 |
| 13.2 | 23 |
| 15.4 | 100 |
| 16.2 | 64 |
| 17.9 | 13 |
| 18.1 | 31 |
| 19.3 | 20 |
| 20.0 | 34 |
| 20.5 | 13 |
| 21.4 | 34 |
| 21.6 | 13 |
| 23.5 | 33 |
| 24.3 | 9 |
| 24.6 | 61 |
| 25.6 | 16 |
| 26.1 | 34 |
| 27.3 | 13 |
| 31.0 | 11 |

TABLE 3-continued

X-Ray powder diffraction peaks of Form C of compound (I).

| Pos. [°2-theta] | Rel. Int. [%] |
|---|---|
| 32.5 | 17 |
| 34.0 | 12 |

Figure 4:
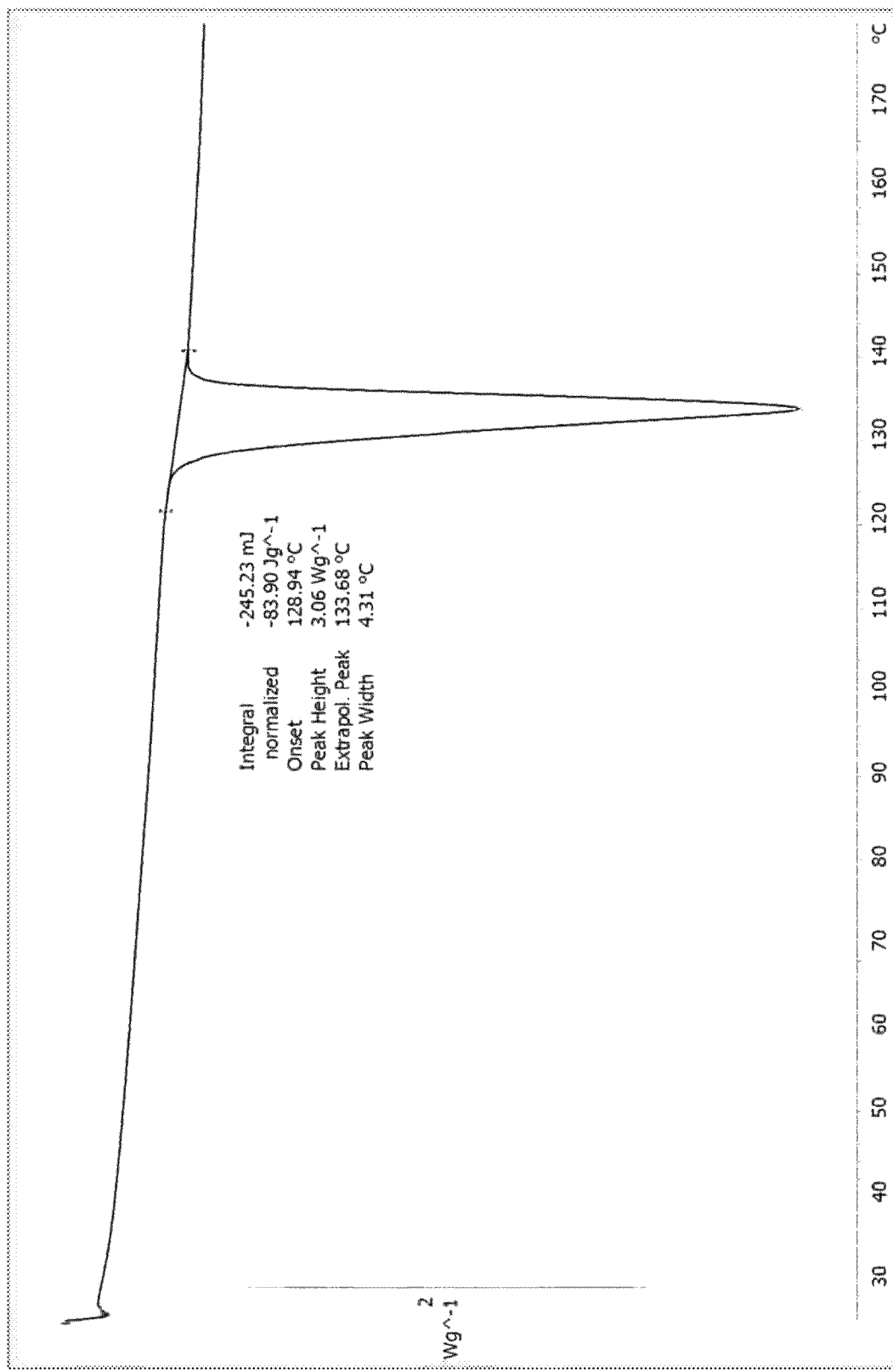
Figure 5:
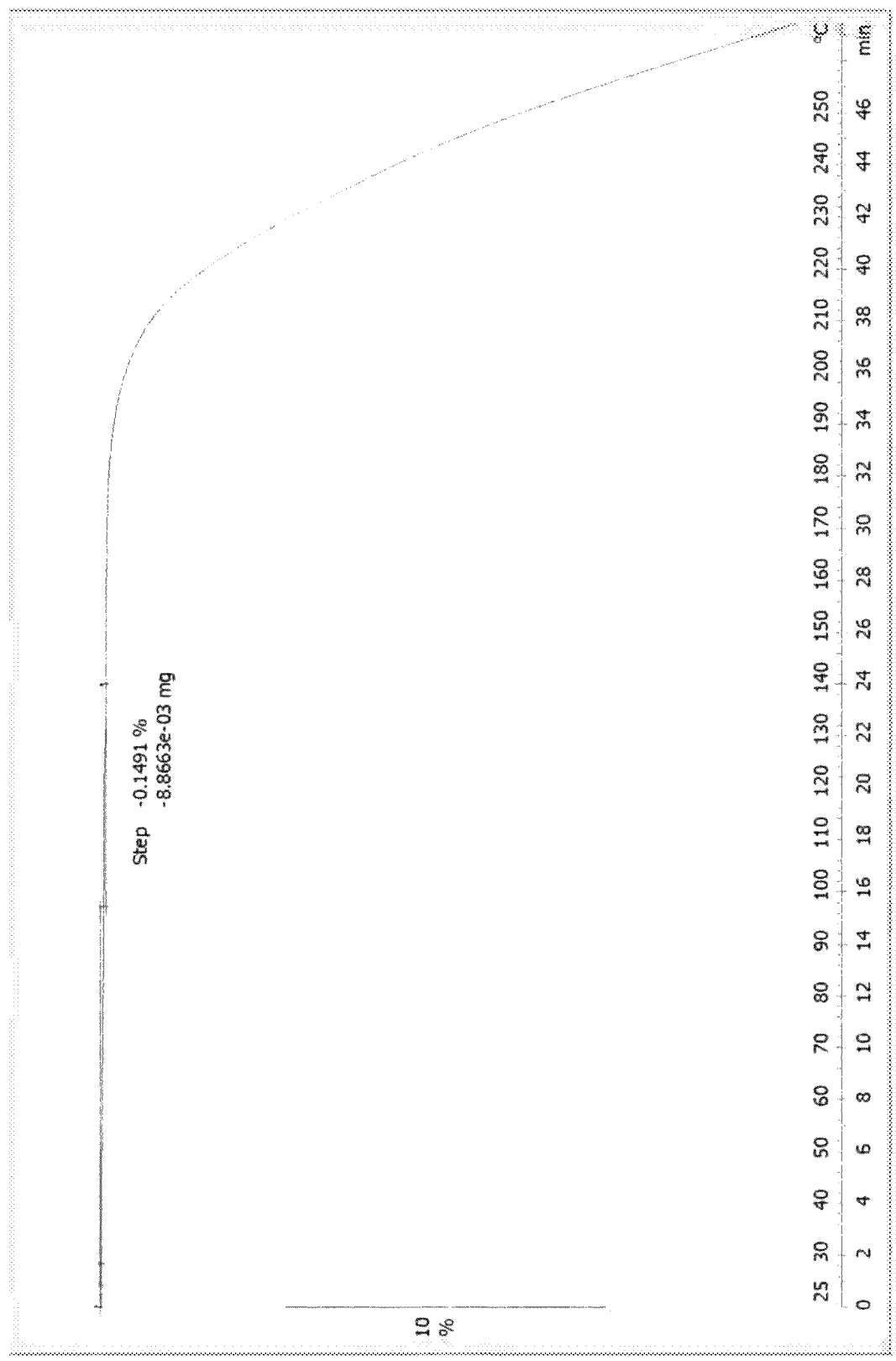

DSC and TGA results shown in FIG. 4 and FIG. 5 indicate Form C of compound (I) has an onset melting temperature at around 128.9° C.

Example 5

Alternative Preparation of Form C of Compound (I).

Approximate 20 mg of Form Amorphous as prepared in Example 1 was weight into a glass vial and approximate 0.05 mL of methanol was added. The obtained solution was agitated at 25° C. overnight. The resulting suspension was centrifuged, the supernatant was removed with a pipette, and the solid residue was further dried by inserting a small strip of filter paper for a few minutes. The solid was collected for XRPD analysis. The XRPD pattern of the solid was the same as that in Table 3 and confirmed to be Form C of compound (I).

Example 6

Alternative Preparation of Form C of Compound (I)

Approximate 100 mg of Form Amorphous as prepared in Example 1 was weighed into a glass vial and approximate 0.05 mL of methanol was added. The resulting suspension was agitated at 25° C. for 2 h, then the solid was collected by filtration and analyzed by XRPD. The XRPD pattern of the solid was same as that in Table 3 and confirmed to be Form C of compound (I).

Example 7

Alternative Preparation of Form C of Compound (I)

Approximate 40 mg of Form Amorphous of compound (I) as prepared in Example 1 was weighed and transferred to a glass vial, to which approximate 0.02 mL of ethanol was added to form a slurry. The vial was mounted to a shaker and kept shaking at 25° C. at 1200 rpm for 2 h. The suspension was filtered and solid was collected for XRPD analysis. The XRPD pattern of solid was same as that in Table 3 and confirmed to be Form C of compound (I).

Example 8

Alternative Preparation of Form C of Compound (I)

Approximate 40 mg of Form Amorphous of compound (I) as prepared in Example 1 was weighed and transferred to a glass vial, to which approximate 0.02 mL of acetone was added to form a slurry. The vial was mounted to a shaker and kept shaking at 25° C. at 1200 rpm for 4 h. The suspension was filtered and solid was collected for XRPD analysis. The XRPD pattern of solid was same as that in Table 3 and confirmed to be Form C of compound (I).

Example 9

Preparation of Form D of Compound (I)

Approximate 2.0 g of Form C of compound (I) as prepared in Example 4 was weighed and transferred to a glass vial, to which 20 mL of ethyl acetate was added to form a suspension. The suspension was filtered, the filtrate was slowly evaporated and solid was collected for XRPD analysis.

Figure 6:
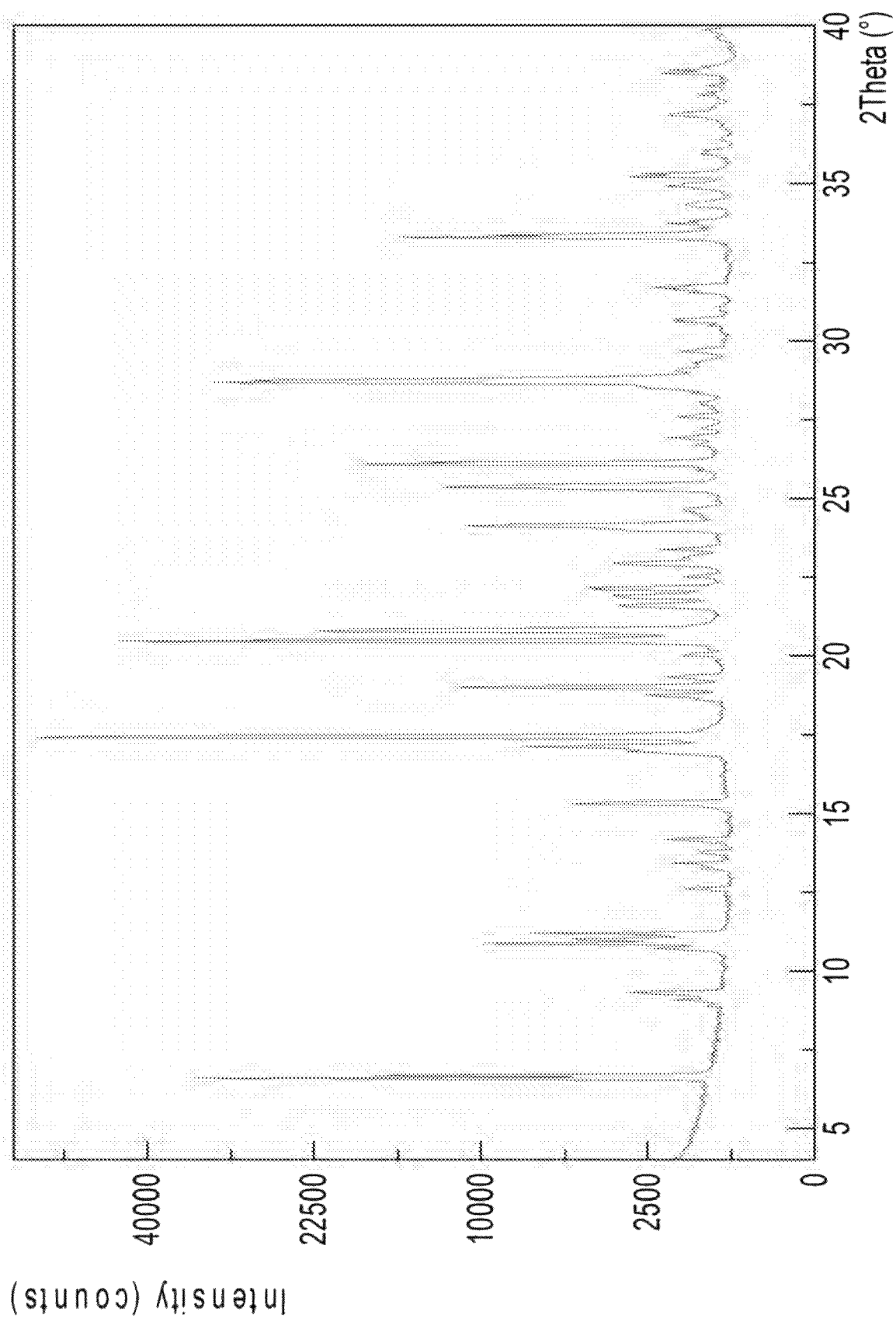

The XRPD pattern of Form D of compound (I) is shown in FIG. 6. Major peaks and their related intensities in the XRPD pattern are shown in Table 4. Form D is an ethyl acetate solvate of compound (I).

Characterization Method:

XRPD: PANalytical EMPYREAN X-ray powder diffractometer with Cu-Kα radiation. Tube voltage was 40 kV and tube current was 40 mA. Scan range was from 4 to 40 degree 2-theta. The step size was 0.0260 at a scanning speed of 3.463°/min.

TABLE 4

X-Ray Powder Diffraction peaks of Form D of compound (I).

| Pos. [°2-theta] | Rel. Int. [%] |
|---|---|
| 6.6 | 67 |
| 9.1 | 2 |
| 9.3 | 5 |
| 10.7 | 3 |
| 10.9 | 19 |
| 11.2 | 12 |
| 12.6 | 2 |
| 13.4 | 2 |
| 13.8 | 1 |
| 14.2 | 3 |
| 15.3 | 9 |
| 17.0 | 4 |
| 17.1 | 14 |
| 17.5 | 100 |
| 18.8 | 3 |
| 19.0 | 21 |
| 19.4 | 2 |
| 20.0 | 1 |
| 20.5 | 63 |
| 20.8 | 43 |
| 21.6 | 5 |
| 21.9 | 5 |
| 22.1 | 7 |
| 22.5 | 1 |
| 22.9 | 5 |
| 23.2 | 1 |
| 23.4 | 2 |
| 24.0 | 5 |
| 24.2 | 18 |
| 24.7 | 1 |
| 25.4 | 22 |
| 26.1 | 30 |
| 26.7 | 1 |
| 26.9 | 2 |
| 27.2 | 1 |
| 27.6 | 2 |
| 28.0 | 1 |
| 28.7 | 58 |
| 29.1 | 2 |
| 29.3 | 1 |
| 29.7 | 2 |
| 30.6 | 2 |
| 31.7 | 3 |
| 33.3 | 28 |
| 33.7 | 2 |
| 34.3 | 2 |
| 34.9 | 2 |
| 35.2 | 5 |
| 35.3 | 3 |
| 35.9 | 1 |

Figure 7:
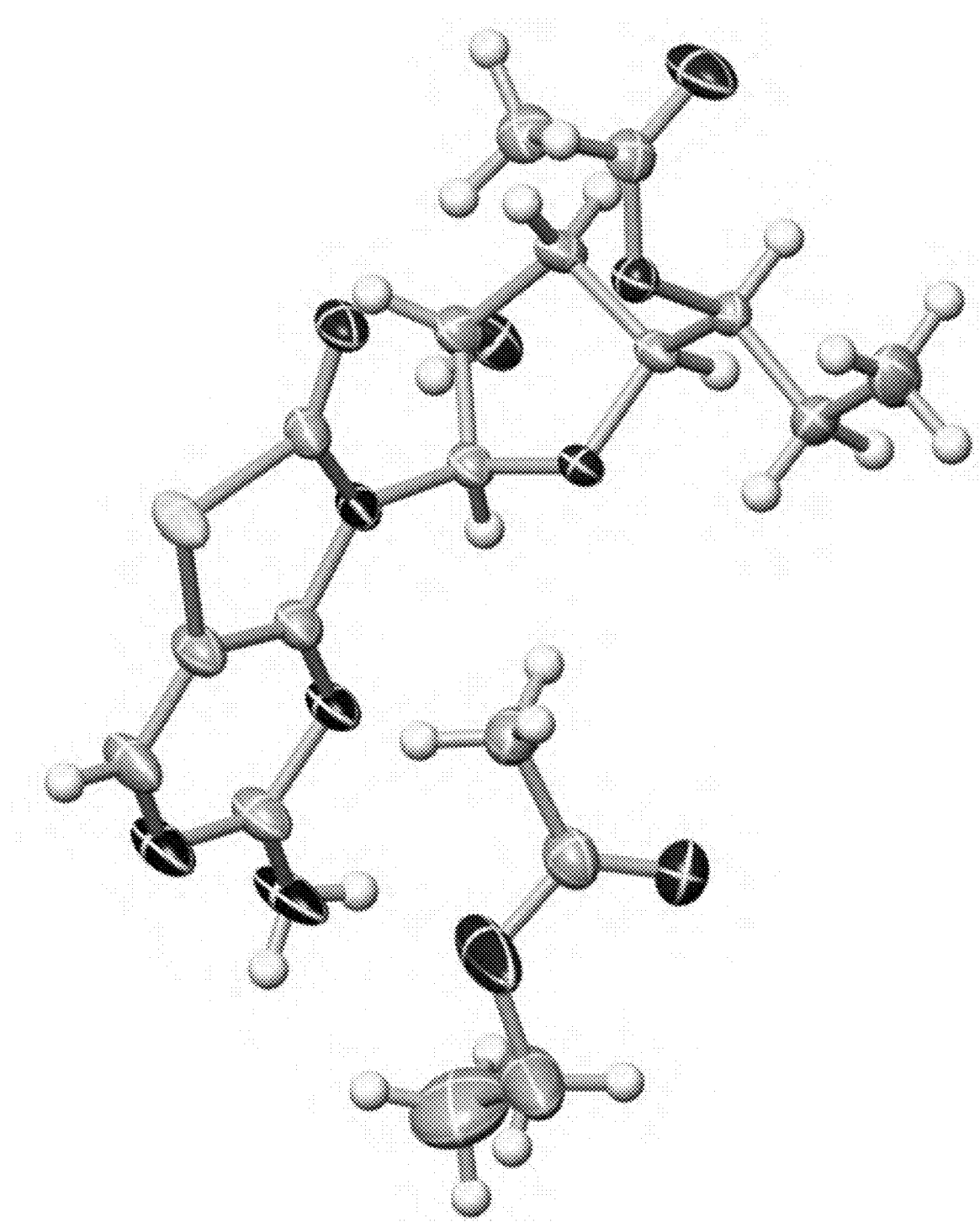

FIG. 7 shows the X-ray structure of ethyl acetate solvate Form D. The single crystal X-ray intensity data were collected at 130(2) K using a Gemini R Ultra diffractometer (Rigaku) with Cu-K-alpha-radiation (1.54184 Å) and processed with the Crysalis package. Structure solution and refinement was performed using the ShelXTL software (Bruker AXS, Karlsruhe). The crystal data and structure refinement is shown in Table 5.

TABLE 5

Single Crystal Structural Data of Forms D

| Crystal form | Form D |
|---|---|
| Solid form description | Ethyl acetate monosolvate |
| Measuring Temperature | 130 K |
| Crystal system | Orthorhombic |
| Space group | P2(1) 2(1) 2(1) |
| Unit cell dimensions | |
| a= | 8.1962 Å |
| b= | 9.8708 Å |
| c= | 26.1518 Å |
| α= | 90° |
| β= | 90° |
| γ= | 90° |
| Cell volume | 2115.76 Å$^3$ |
| API molecules in unit cell | 4 |
| Calculated density | 1.389 g/cm$^3$ |

Example 10

Preparation of Form A of Compound (I)

Figure 8:
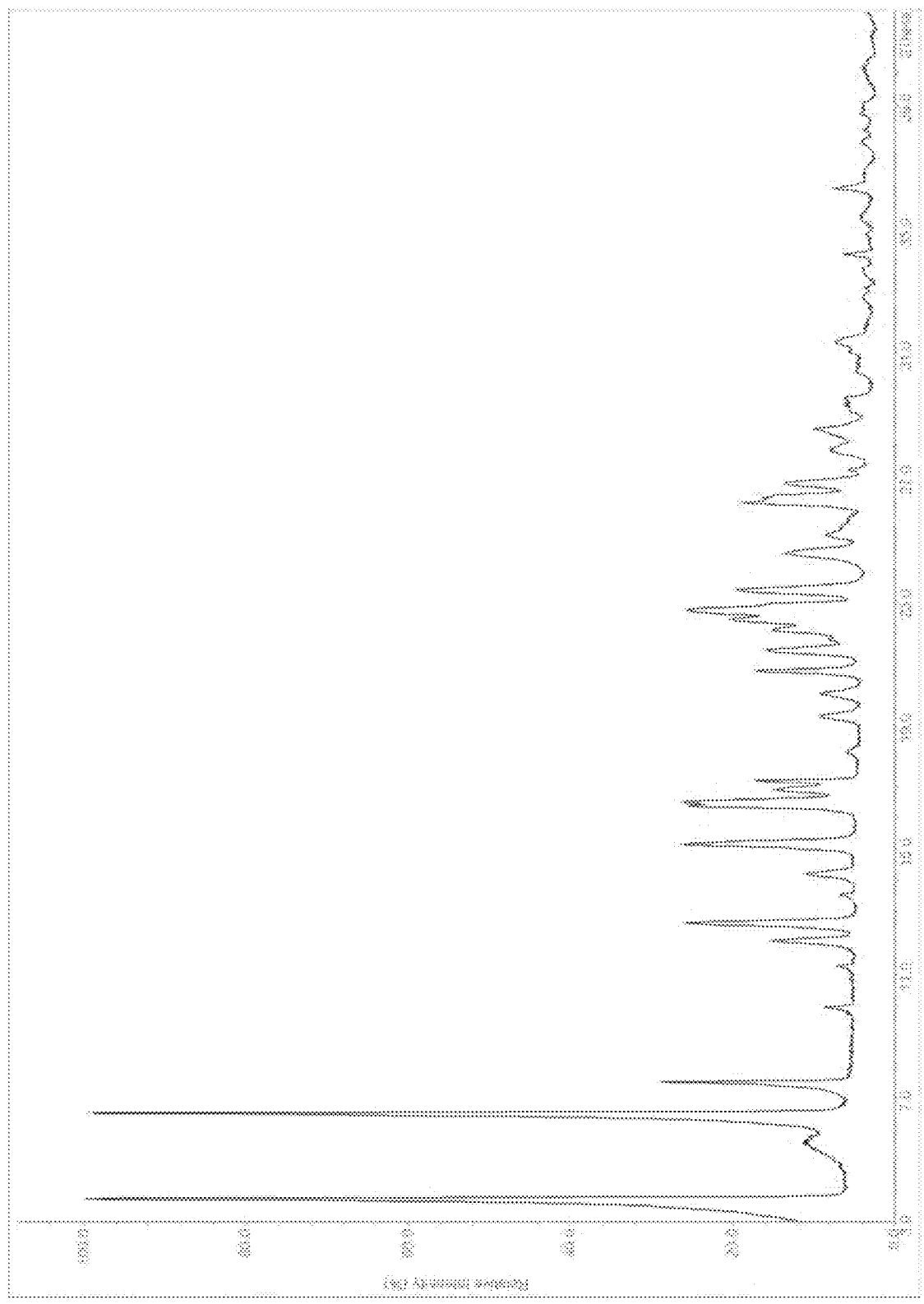

1000 mg of Form Amorphous of compound (I) was weighed and transferred to a glass vial then 0.3 mL, of acetonitrile was added to form a slurry. The vial was mounted to a shaker and kept shaking for 4 hours 25° C. at 1200 rpm. The suspension was filtered and the solid was collected for XRPD analysis. The XRPD pattern of Form A of compound (I) is shown in FIG. 8. Major peaks and their related intensities in the XRPD pattern are shown in Table 6. Depending on the solvation status Form A can be a solvate, a hydrate or a polymorph of compound (I).

Characterization Method:

DSC analysis: TA Q2000, 30-200° C., heating rate 10° C./min.

XRPD: X-ray diffraction patterns were recorded at ambient conditions in transmission geometry with a STOE STADI P diffractometer with Cu-Kα1 radiation. The diffractometer was equipped with a primary Ge beam monochromator and a silicon strip detector. Tube voltage was 40 KV and tube current was 40 mA. Scan range was from 3 to 42 degree 2-theta. The step size was 0.02 degree 2-theta with a measurement time of 20 s per step.

TABLE 6

X-Ray Powder Diffraction peaks of Form A of compound (I).

| Pos. [°2-theta] | Rel. Int. [%] |
|---|---|
| 3.7 | 100 |
| 6.5 | 99 |
| 7.5 | 24 |
| 9.9 | 4 |
| 11.2 | 2 |
| 12.1 | 11 |
| 12.6 | 22 |
| 13.5 | 2 |
| 14.2 | 7 |
| 15.2 | 23 |
| 16.4 | 22 |
| 16.5 | 23 |
| 16.9 | 11 |
| 17.2 | 14 |
| 18.2 | 2 |
| 19.3 | 5 |
| 20.0 | 5 |
| 20.8 | 14 |

TABLE 6-continued

X-Ray Powder Diffraction peaks of Form A of compound (I).

| Pos. [°2-theta] | Rel. Int. [%] |
|---|---|
| 21.4 | 12 |
| 21.8 | 4 |
| 22.1 | 12 |
| 22.4 | 17 |
| 22.7 | 23 |
| 23.4 | 16 |
| 24.6 | 10 |
| 25.1 | 5 |
| 26.2 | 16 |
| 26.8 | 10 |
| 27.2 | 2 |
| 27.9 | 5 |
| 28.5 | 7 |
| 31.0 | 3 |
| 31.3 | 5 |
| 34.2 | 4 |
| 36.3 | 5 |
| 37.8 | 2 |
| 38.2 | 1 |
| 38.7 | 2 |

Figure 12:
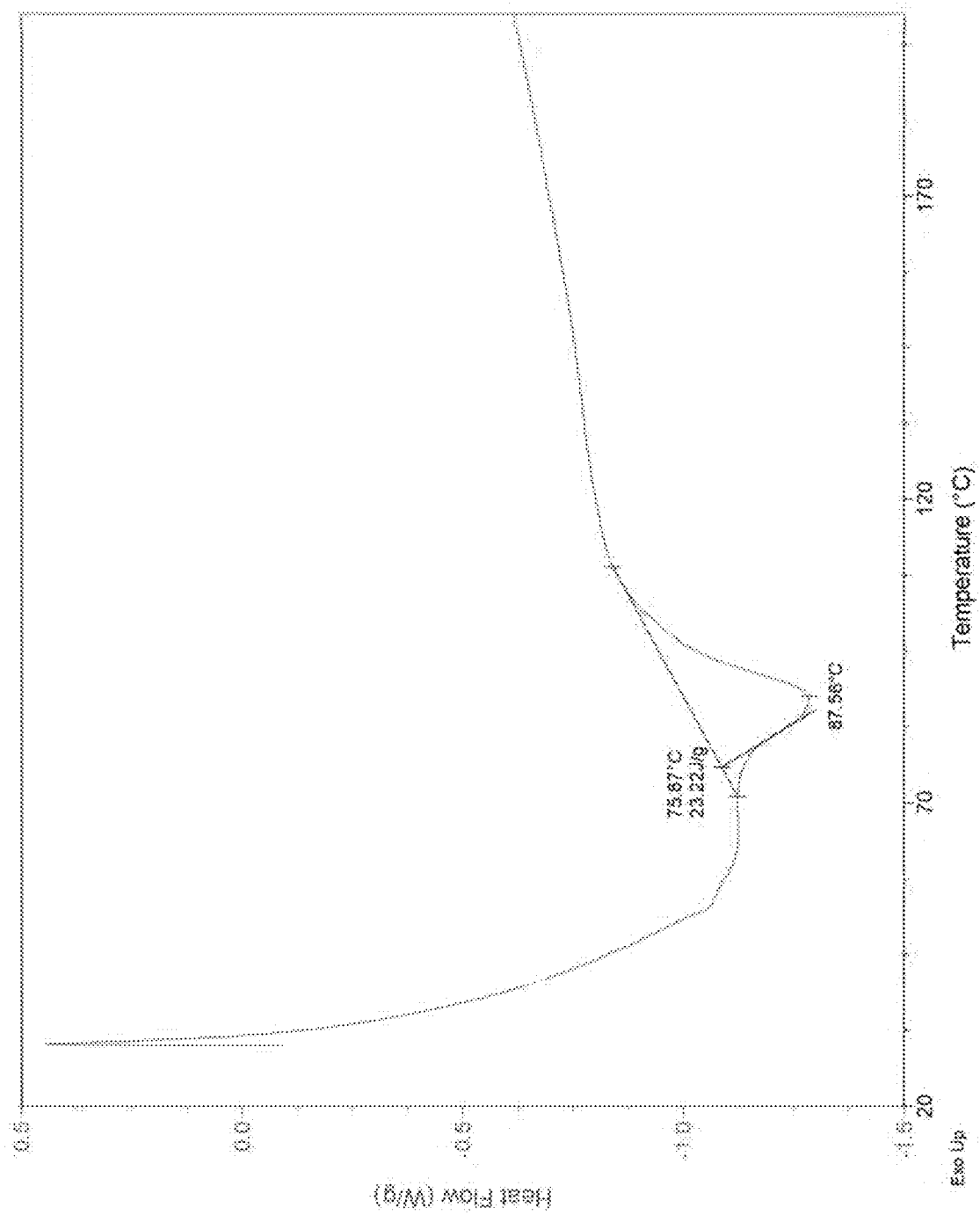

DSC result shown in FIG. 12 indicates Form A of compound (I) has an onset of endothermal event at around 75.9° C.

Example 11

Preparation of Form B of Compound (I)

Figure 9:
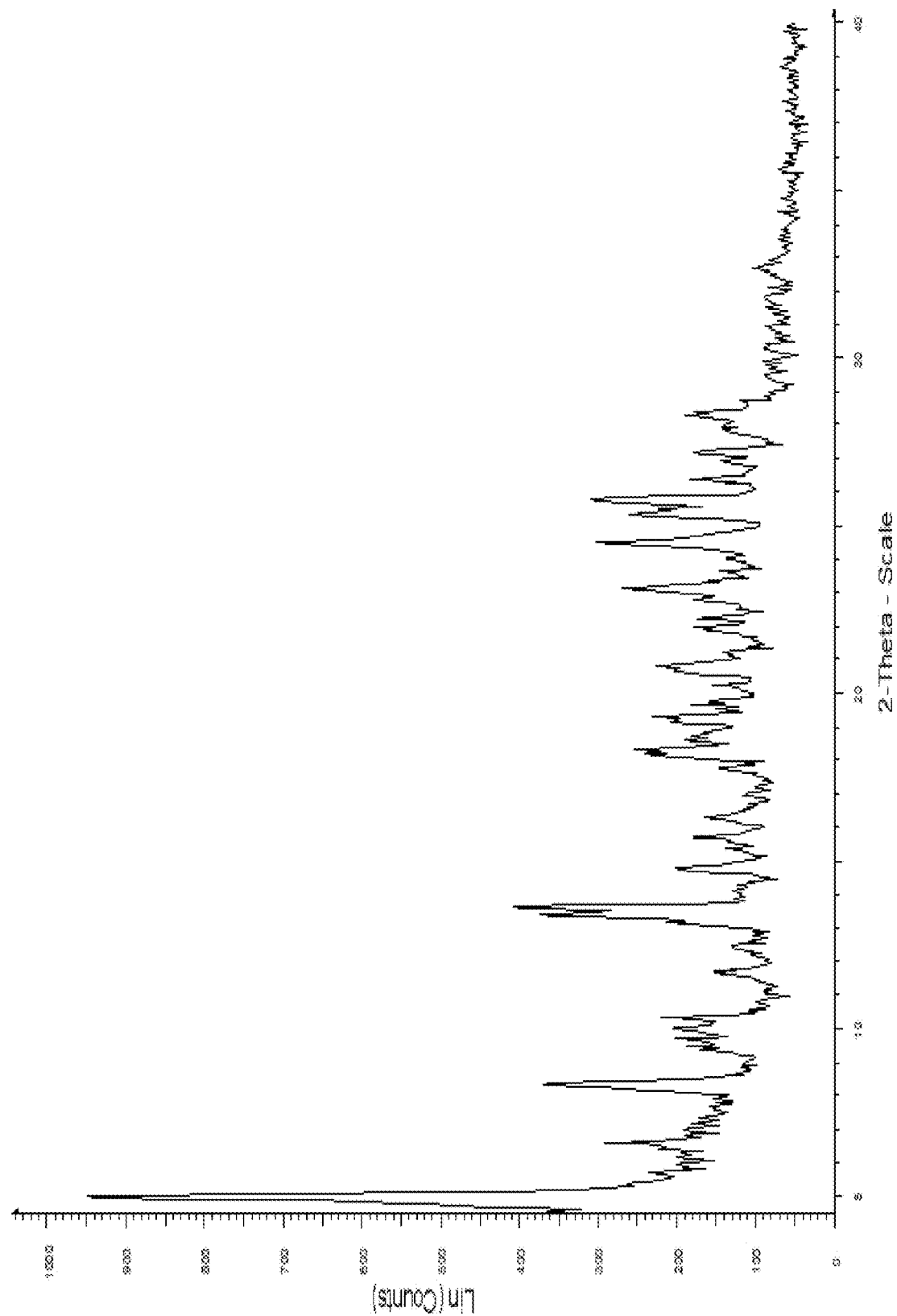

Form A as prepared in Example 10 was suspended in water to form a slurry at room temperature for 2 hours to afford Form B, then the solid was collected by filtration and dried under vacuum. Form B was characterized by XRPD shown in FIG. 9. Major peaks and their related intensities in the XRPD pattern are shown in Table 7. Depending on the solvation status Form B can be a solvate, a hydrate or a polymorph of compound (I).

Characterization Method:

DSC analysis: TA Q2000, 30-200° C., heating rate 10° C./min.

XRPD: For crystalline form analysis, sample was mounted in a sample holder on a goniometer and measured at ambient conditions. Data were collected at 2-theta from 4 to 400 with a step size of 0.05° and a scanning speed of 1 s/step on a Bruker D8 Advance X-ray powder diffractometer at 40 kV and 40 mA. Cu-radiation of 1.54 Å wavelength was used for data collection.

TABLE 7

X-Ray Powder Diffraction peaks of Form B of compound (I).

| Pos. [°2-theta] | Rel. Int. [%] |
|---|---|
| 4.9 | 100 |
| 6.5 | 30 |
| 8.3 | 36 |
| 10.0 | 21 |
| 10.3 | 21 |
| 13.3 | 40 |
| 13.6 | 42 |
| 14.7 | 21 |
| 15.7 | 18 |
| 16.2 | 18 |
| 17.8 | 17 |
| 18.3 | 27 |
| 19.3 | 27 |
| 20.6 | 23 |
| 21.9 | 19 |

TABLE 7-continued

X-Ray Powder Diffraction peaks of Form B of compound (I).

| Pos. [°2-theta] | Rel. Int. [%] |
|---|---|
| 22.3 | 21 |
| 23.1 | 30 |
| 24.5 | 32 |
| 25.3 | 30 |
| 25.9 | 37 |
| 27.2 | 19 |

Figure 13:
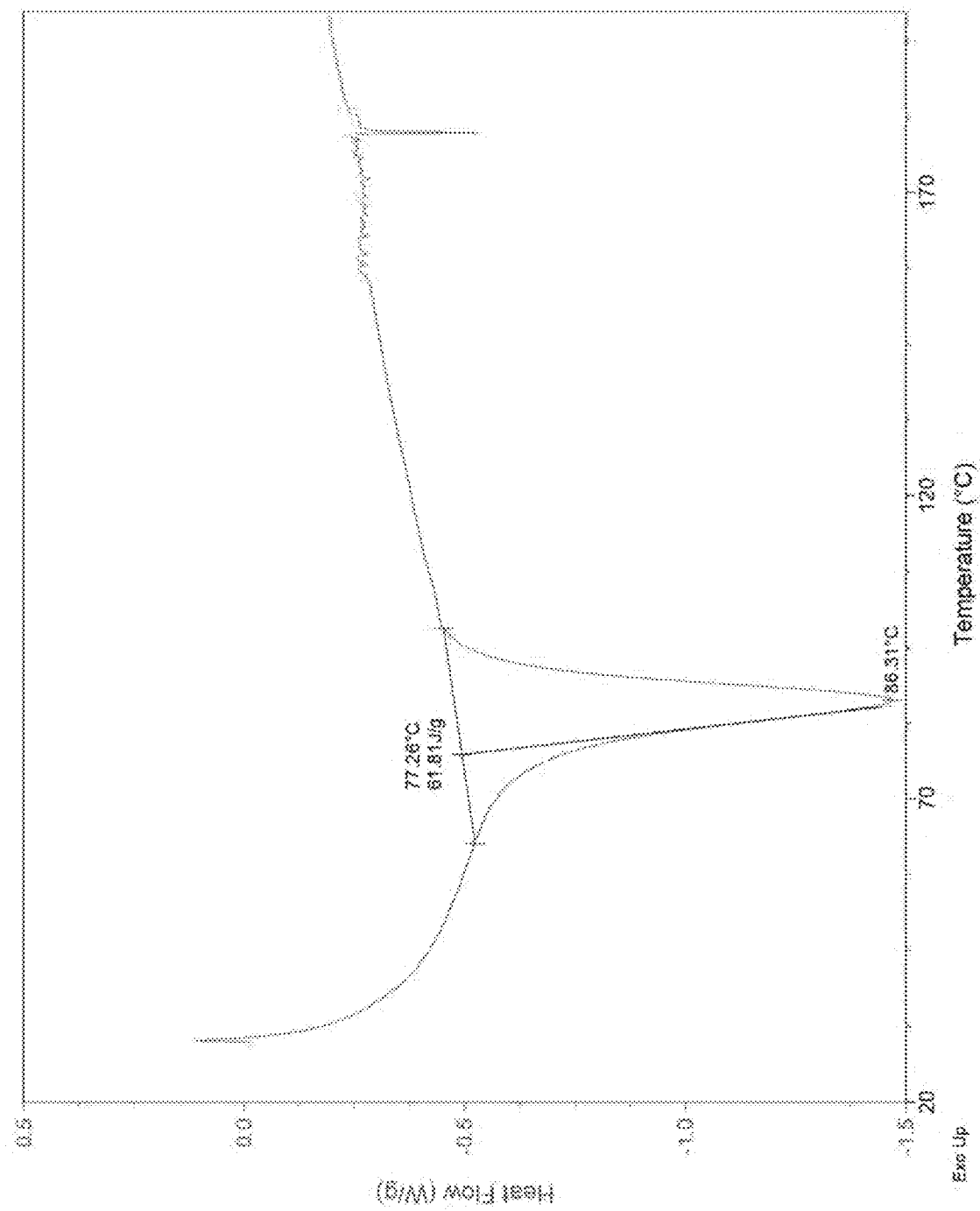

DSC result shown in FIG. 13 indicates Form B of compound (I) has an onset of endothermal event at around 77.3° C.

Example 12

Preparation of Form G of Compound (I)

Figure 10:
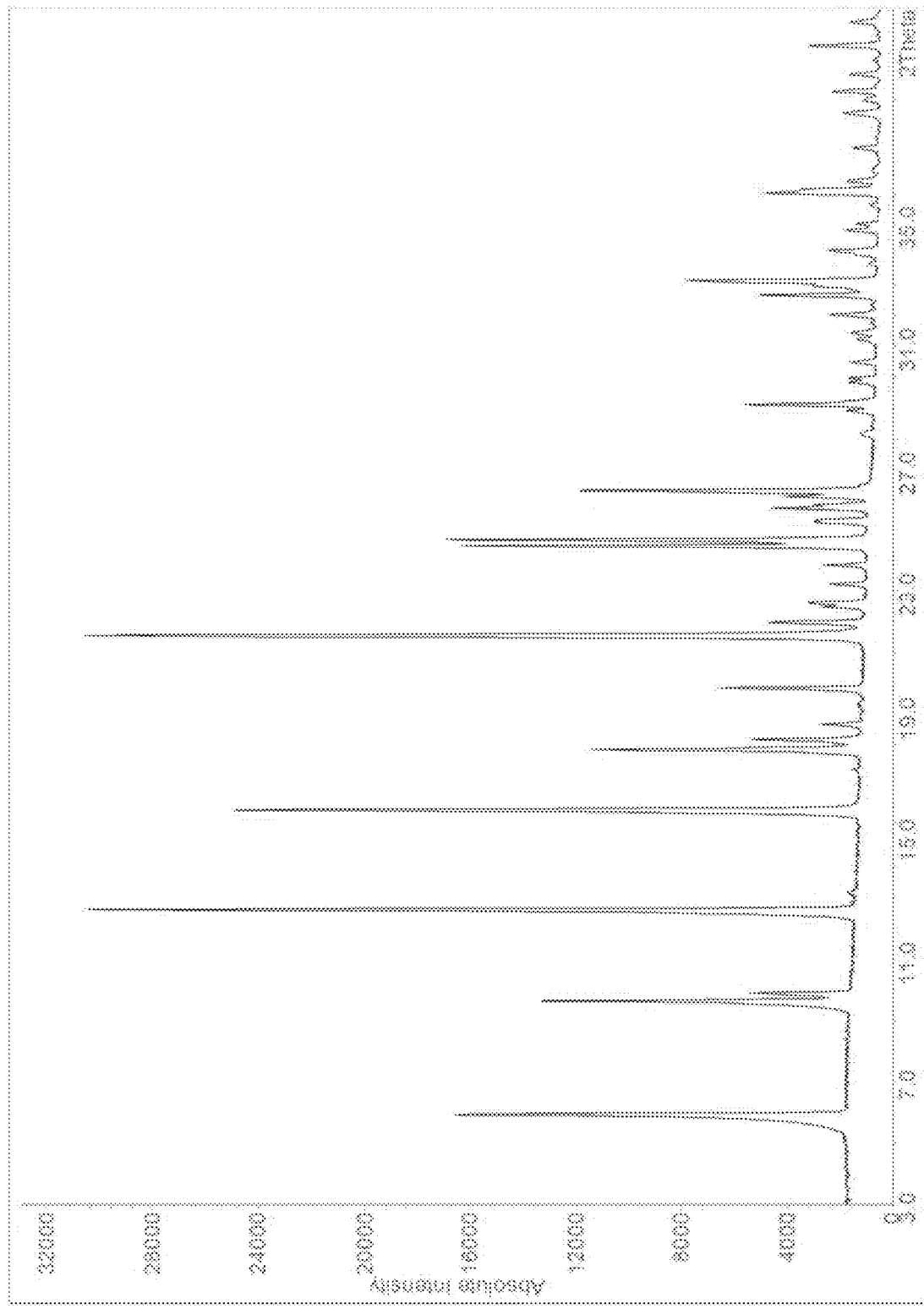

15 g of compound (I) was suspended at ambient temperature in 44.4 g of acetone. The suspension was heated to 60° C. until complete dissolution was achieved. The dark yellow solution was cooled from 60° C. to 15° C. within approx. 1 hour. At 15° C. the solution was polish filtered and added to 112.8 g of n-heptane (pre-cooled to 15° C.) while stirring. The resulting suspension was stirred for 3 days at 15° C. before the solid was isolated by filtration. Form G was characterized by XRPD shown in FIG. 10. Major peaks and their related intensities in the XRPD pattern are shown in Table 8. Single crystal data can be found in Table 9. Form G is a polymorph of compound (I).

Characterization Method:

DSC analysis: Mettler Toledo DSC 2, 25-200° C., heating rate 10° C./min.

XRPD: X-ray diffraction patterns were recorded at ambient conditions in transmission geometry with a Stoe Stadi P diffractometer (Cu Kα1 radiation (1.5406 Å), 40 kV and 40 mA, primary beam monochromator, silicon strip detector, angular range 3° to 42° 2-theta with a step size of 0.02° 2-theta, approximately 30 minutes total measurement time). The samples were prepared and analyzed without further processing (e.g. grinding or sieving) of the substance.

TABLE 8

X-Ray Powder Diffraction peaks of Form G of compound (I).

| Pos. [°2-theta] | Rel. Int. [%] |
|---|---|
| 5.9 | 49 |
| 9.6 | 40 |
| 9.9 | 12 |
| 12.6 | 97 |
| 15.9 | 80 |
| 17.9 | 34 |
| 18.2 | 14 |
| 19.9 | 19 |
| 21.6 | 100 |
| 22.0 | 12 |
| 24.5 | 52 |
| 24.7 | 51 |
| 25.8 | 12 |
| 26.1 | 11 |
| 26.3 | 38 |
| 29.1 | 17 |
| 32.7 | 15 |
| 33.1 | 24 |

Figure 14:
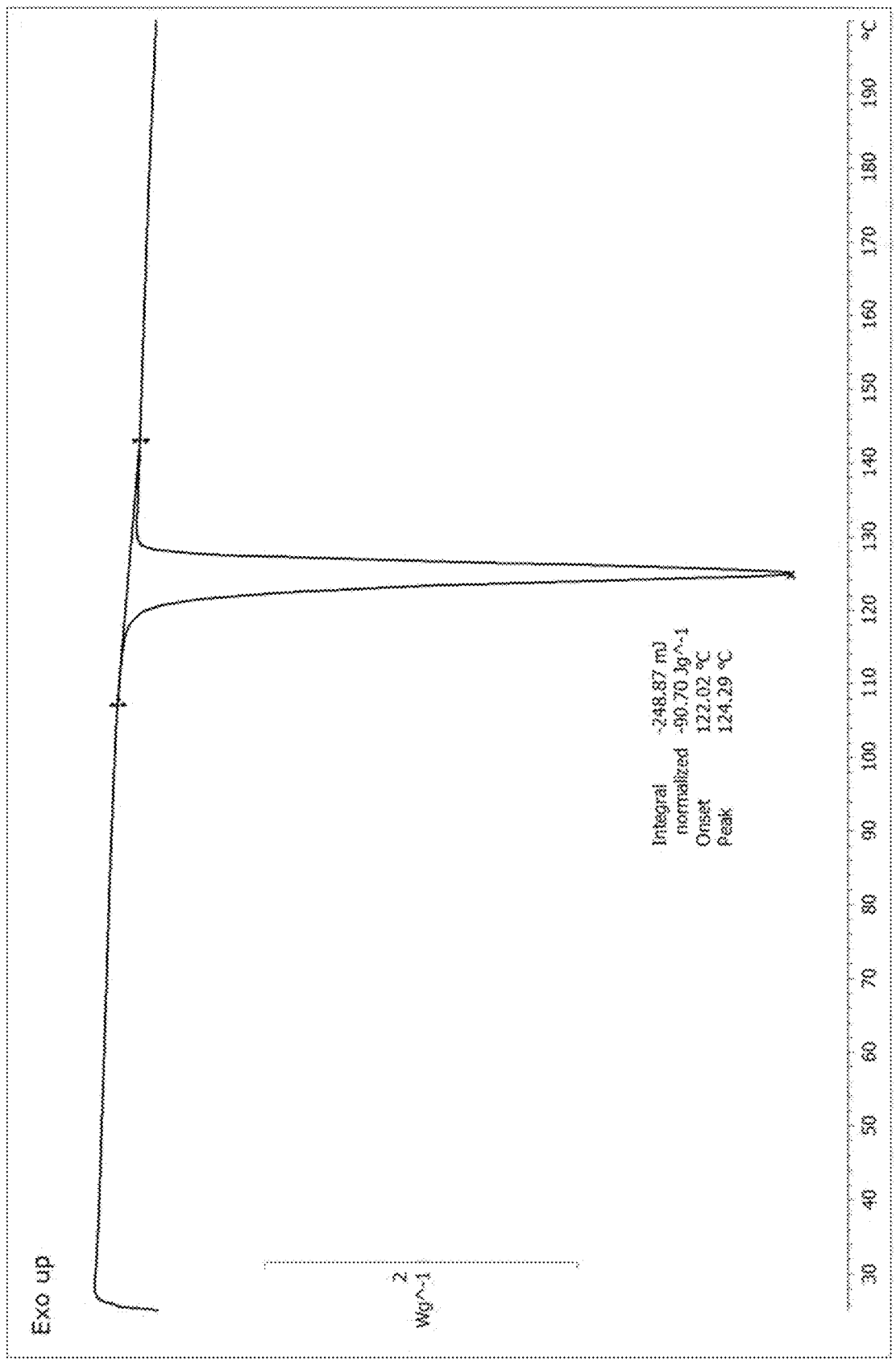

DSC result shown in FIG. 14 indicates Form G of compound (I) has an onset melting temperature at around 122.0° C.

Single crystal diffraction: A single crystal was mounted in a loop and cooled to 100 K in a nitrogen stream. Data were collected at the Swiss light source beam line X10SA using a Pilatus detector with synchrotron radiation (0.70 Å) and data processed with the program XDS. The crystal structure was solved and refined with the program ShelXTL (Bruker AXS, Karlsruhe).

TABLE 9

Single Crystal Structural Data of Form G

| Crystal form | Form G |
|---|---|
| Solid form description | free form |
| Measuring Temperature | 100(2) K |
| Crystal system | Monoclinic |
| Space group | C2 |
| Unit cell dimensions | |
| a= | 30.543(6) Å |
| b= | 5.5530(11) Å |
| c= | 9.4980(19) Å |
| α= | 90° |
| β= | 105.10(3)° |
| γ= | 90° |
| Cell volume | 1555.3(6) Å$^3$ |
| API molecules in unit cell | 4 |
| Calculated density | 1.513 g/cm$^3$ |

Example 13

Preparation of Form F of Compound (I)

101.1 mg of Form C of compound (I) was suspended in 1 mL of water. The suspension was tumbled at 60° C. for 22 days, and the solid was isolated as Form F by filtration. The product was dried for 4 days in a vacuum oven at 50° C./5 mbar.

Figure 16:
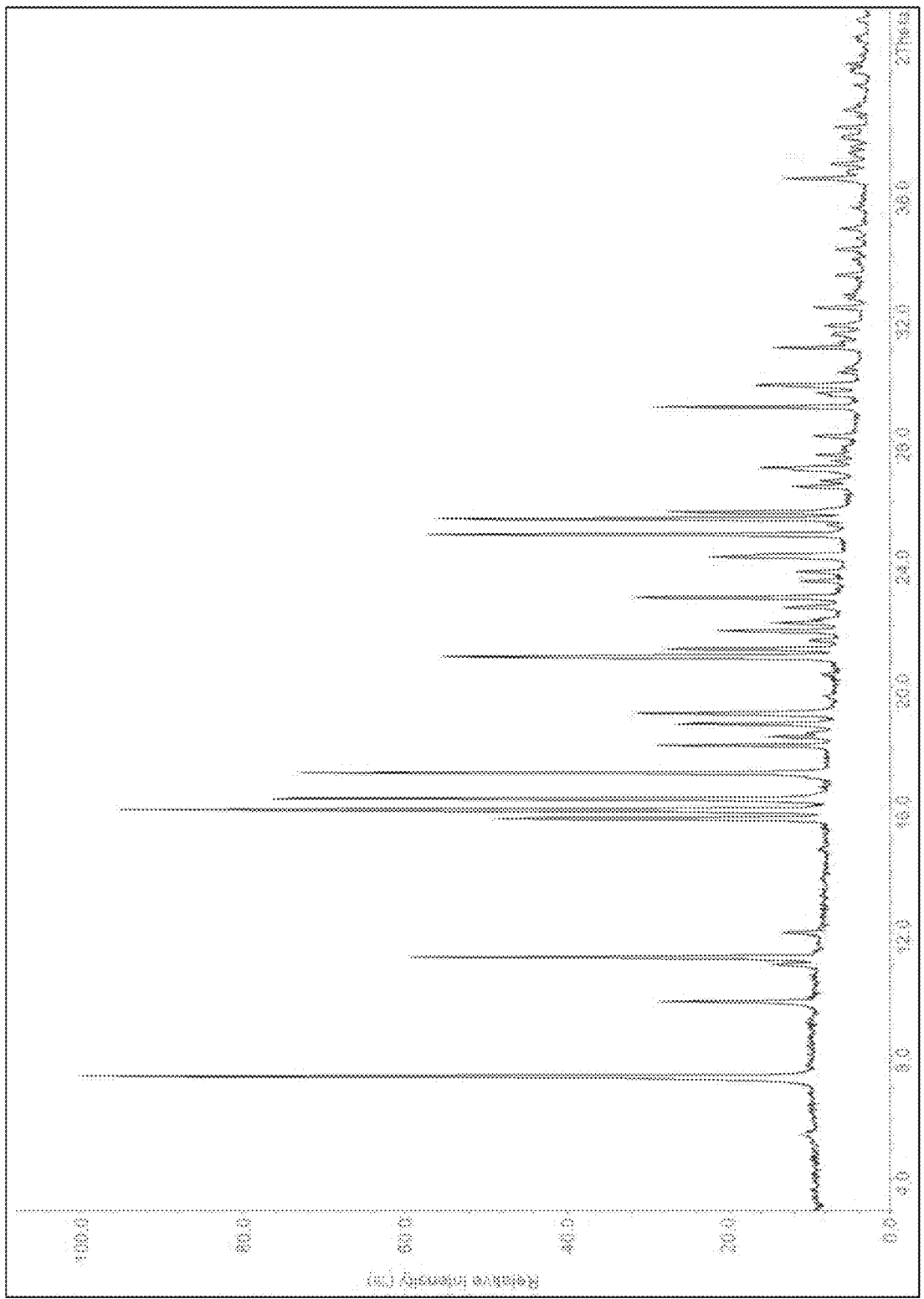

The XRPD pattern of Form F of compound (I) is shown in FIG. 16. Major peaks and their related intensities in the XRPD pattern are shown in Table 10. Form F is a polymorph of compound (I).

Characterization Method:

DSC analysis: Mettler Toledo DSC 2, 25-200° C., heating rate 10° C./min.

XRPD: X-ray diffraction patterns were recorded at ambient conditions in transmission geometry with a Stoe Stadi P diffractometer (Cu Kα1 radiation (1.5406 Å), 40 kV and 40 mA, primary beam monochromator, silicon strip detector, angular range 3° to 42° 2-theta with a step size of 0.02° 2-theta, approximately 30 minutes total measurement time). The samples were prepared and analyzed without further processing (e.g. grinding or sieving) of the substance.

TABLE 10

X-Ray Powder Diffraction peaks of Form F of compound (I).

| Pos. [°2-theta] | Rel. Int. [%] |
|---|---|
| 7.4 | 100 |
| 9.8 | 21 |
| 11.0 | 7 |
| 11.2 | 57 |
| 12.0 | 6 |
| 15.7 | 45 |
| 16.0 | 98 |
| 16.4 | 78 |
| 17.2 | 74 |
| 18.1 | 24 |
| 18.4 | 9 |
| 18.8 | 22 |
| 19.2 | 27 |

TABLE 10-continued

X-Ray Powder Diffraction peaks of Form F of compound (I).

| Pos. [°2-theta] | Rel. Int. [%] |
| --- | --- |
| 21.0 | 54 |
| 21.2 | 24 |
| 21.8 | 17 |
| 22.1 | 9 |
| 22.6 | 8 |
| 22.9 | 29 |
| 24.2 | 19 |
| 25.0 | 59 |
| 25.5 | 56 |
| 25.7 | 25 |
| 26.5 | 8 |
| 27.1 | 12 |
| 29.1 | 27 |
| 29.8 | 14 |
| 31.0 | 12 |
| 32.3 | 7 |
| 36.5 | 11 |

Figure 15:
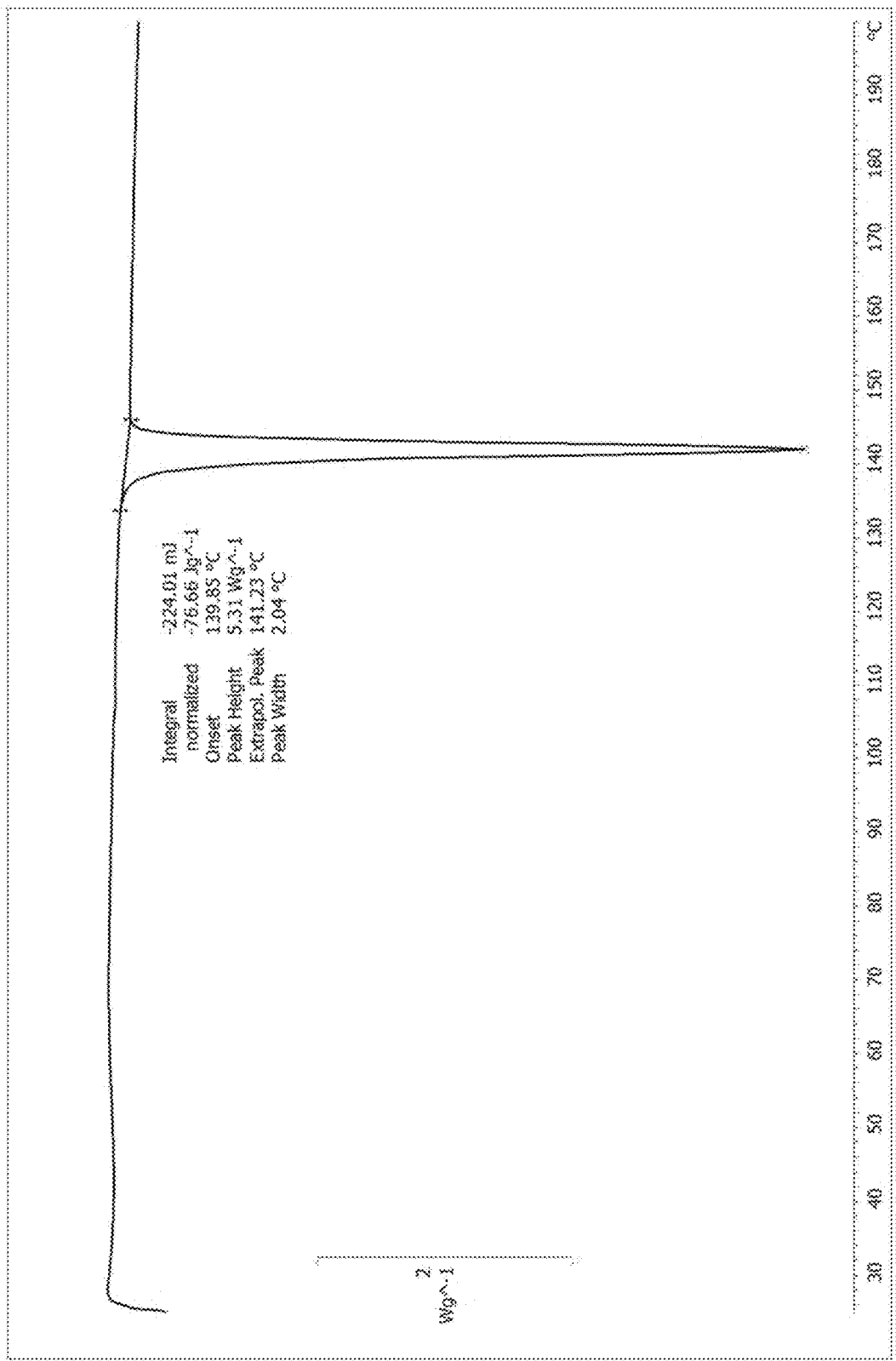

DSC result shown in FIG. 15 indicates Form F of compound (I) as an onset melting temperature at around 141.2° C.

Example 14

Preparation of Form H of Compound (I)

153.5 mg of Form C of compound (I) was dissolved in 2.85 mL of dimethyl carbonate at ambient temperature. The solution was filtered (0.45 μm PTFE filter). 6.3 mL of n-heptane was added and precipitation was observed. The suspension was stirred for one day at 22° C. The solid was isolated as Form H by filtration and dried for 2 days in a vacuum oven at 50° C./5 mbar.

Figure 17:
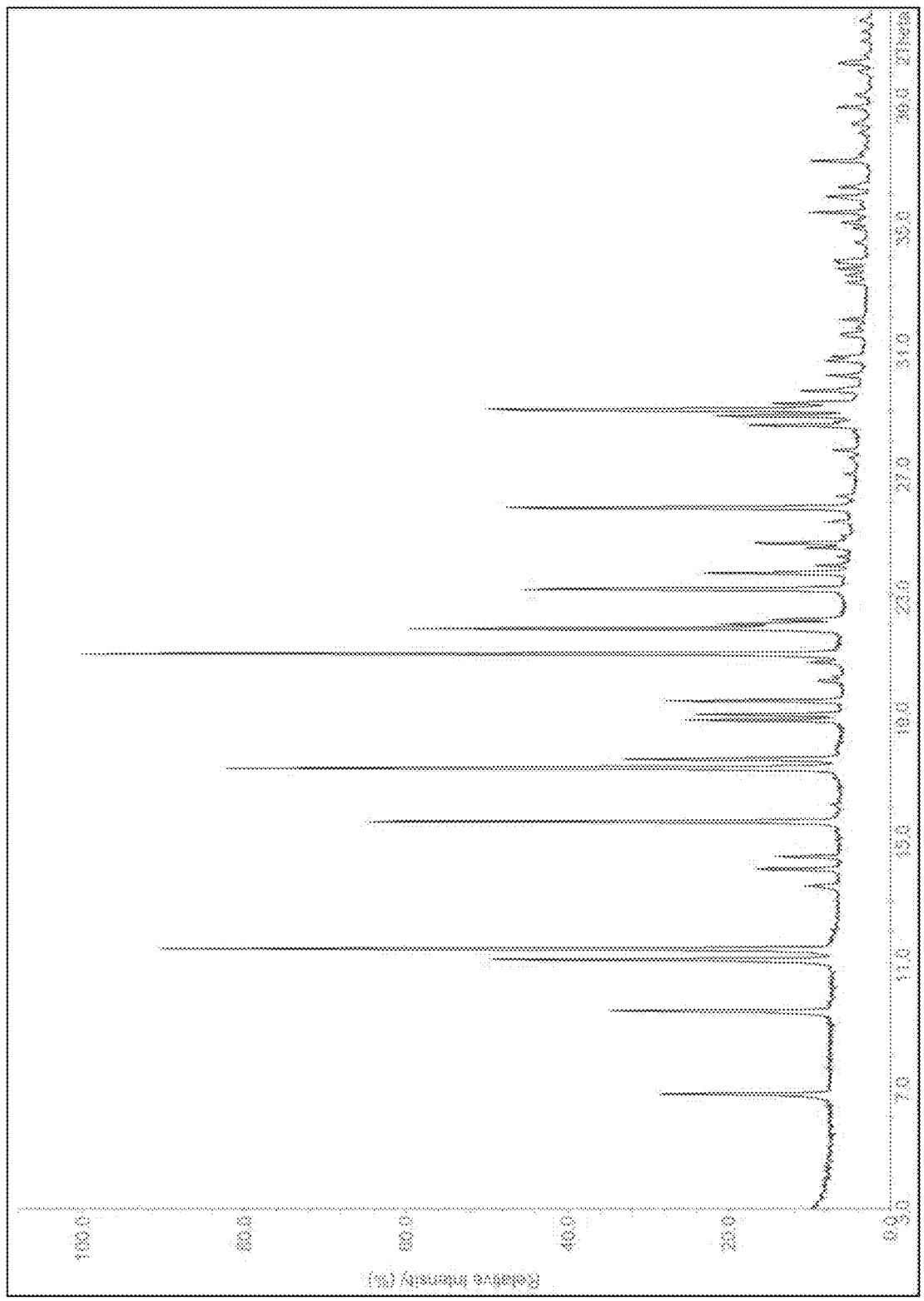

The XRPD pattern of Form H of compound (I) is shown in FIG. 17. Major peaks and their related intensities in the XRPD pattern are shown in Table 11. Form H is a dimethyl carbonate solvate of compound (I).

Characterization Method:

XRPD: X-ray diffraction patterns were recorded at ambient conditions in transmission geometry with a Stoe Stadi P diffractometer (Cu Kα1 radiation (1.5406 Å), 40 kV and 40 mA, primary beam monochromator, silicon strip detector, angular range 3° to 42° 2-theta with a step size of 0.02° 2-theta, approximately 30 minutes total measurement time). The samples were prepared and analyzed without further processing (e.g. grinding or sieving) of the substance.

TABLE 11

X-Ray Powder Diffraction peaks of Form H of compound (I).

| Pos. [°2-theta] | Rel. Int. [%] |
| --- | --- |
| 6.7 | 21 |
| 9.4 | 29 |
| 11.1 | 45 |
| 11.4 | 88 |
| 14.0 | 11 |
| 14.4 | 8 |
| 15.6 | 61 |
| 17.3 | 78 |
| 17.6 | 29 |
| 18.9 | 20 |
| 19.1 | 19 |
| 19.5 | 23 |
| 20.8 | 5 |
| 21.1 | 100 |
| 21.9 | 56 |
| 22.0 | 16 |
| 22.2 | 10 |
| 23.2 | 43 |
| 23.7 | 19 |
| 24.7 | 13 |
| 25.8 | 46 |
| 28.5 | 15 |
| 28.8 | 19 |
| 29.0 | 48 |
| 29.2 | 12 |
| 29.6 | 8 |
| 30.1 | 5 |
| 30.6 | 5 |
| 35.4 | 8 |
| 36.0 | 6 |
| 37.1 | 8 |
| 38.9 | 5 |

Single crystal diffraction: A single crystal was mounted in a loop and cooled to 100 K in a nitrogen stream. Data were collected at the Swiss light source beam line X10SA using a Pilatus detector with synchrotron radiation (0.70 Å) and data processed with the program XDS. The crystal structure was solved and refined with the program ShelXTL (Bruker AXS, Karlsruhe).

TABLE 12

Single Crystal Structural Data of Form H

| Crystal form | Form H |
| --- | --- |
| Solid form description | free form |
| Measuring Temperature | 100(2) K |
| Crystal system | orthorhombic |
| Space group | P2(1)2(1)2(1) |
| Unit cell dimensions | |
| a= | 8.0750(16) Å |
| b= | 10.056(2) Å |
| c= | 26.160(5) Å |
| α= | 90° |
| β= | 90° |
| γ= | 90° |
| Cell volume | 2124.2(7) Å$^3$ |
| API molecules in unit cell | 4 |
| Calculated density | 1.390 g/cm$^3$ |

Example 15

Preparation of Form I of Compound (I)

Approximately 306 mg of compound (I) (Form C) was suspended in 1.5 mL of methyl ethyl ketone. The suspension was tumbled at 22° C. for 55 days. The solid was isolated as Form I by filtration and dried overnight at ambient temperature at 400 mbar.

Figure 18:
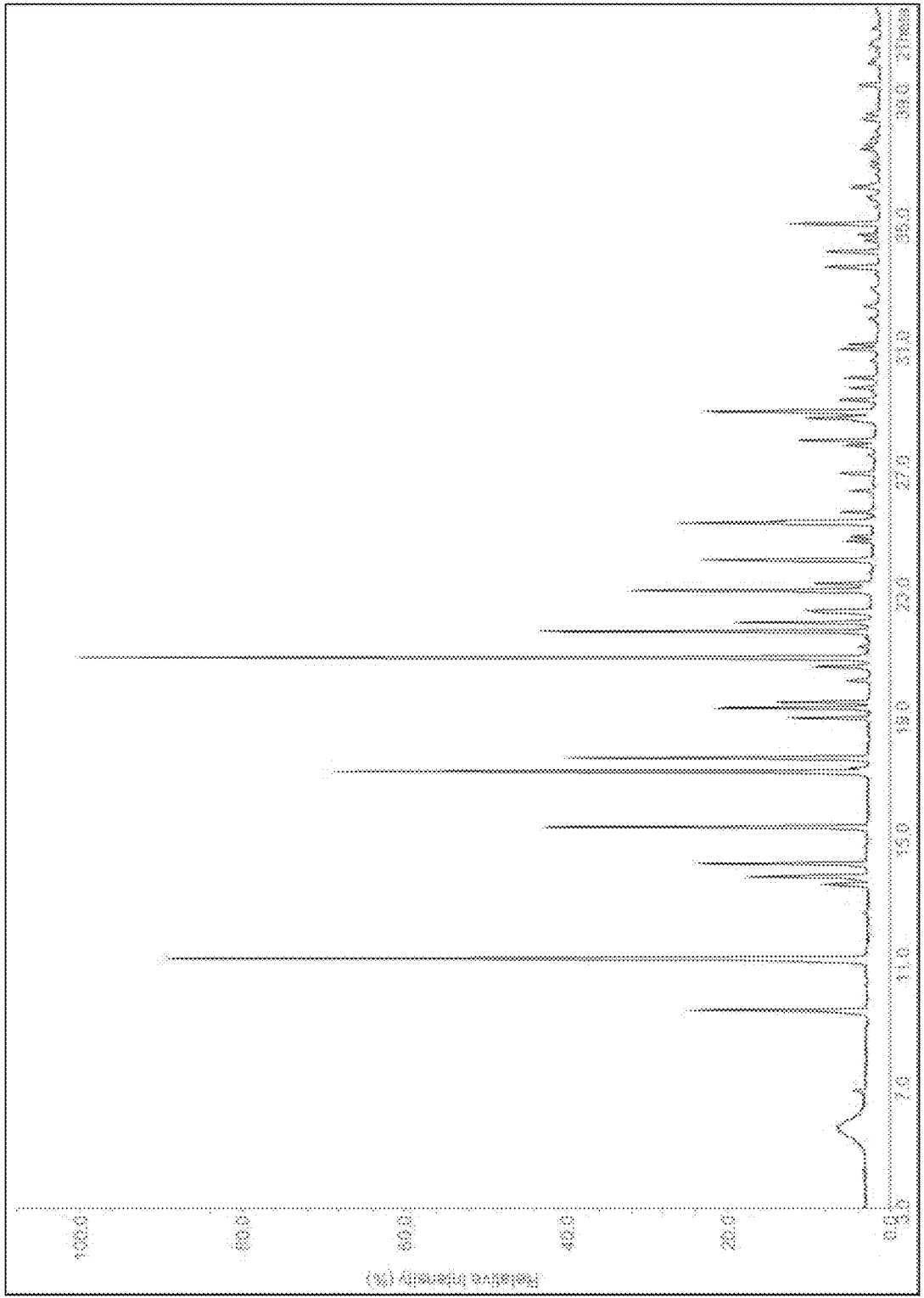

The XRPD pattern of Form I of compound (I) is shown in FIG. 18. Major peaks and their related intensities in the XRPD pattern are shown in Table 13. Form I is a methyl ethyl ketone solvate of compound (I).

Characterization Method:

XRPD: X-ray diffraction patterns were recorded at ambient conditions in transmission geometry with a Stoe Stadi P diffractometer (Cu Kα1 radiation (1.5406 Å), 40 kV and 40 mA, primary beam monochromator, silicon strip detector, angular range 3° to 42° 2-theta with a step size of 0.02° 2-theta, approximately 30 minutes total measurement time). The samples were prepared and analyzed without further processing (e.g. grinding or sieving) of the substance.

TABLE 13

X-Ray Powder Diffraction peaks of Form I of compound (I).

| Pos. [°2-theta] | Rel. Int. [%] |
|---|---|
| 9.4 | 23 |
| 11.1 | 94 |
| 13.5 | 6 |
| 13.8 | 16 |
| 14.2 | 22 |
| 15.4 | 43 |
| 17.2 | 66 |
| 17.6 | 40 |
| 18.9 | 10 |
| 19.2 | 21 |
| 19.4 | 13 |
| 20.6 | 8 |
| 20.9 | 100 |
| 21.7 | 42 |
| 22.0 | 18 |
| 22.4 | 8 |
| 23.0 | 33 |
| 23.3 | 8 |
| 24.0 | 22 |
| 25.2 | 25 |
| 25.3 | 14 |
| 25.6 | 4 |
| 26.9 | 5 |
| 27.9 | 11 |
| 28.7 | 9 |
| 28.9 | 23 |
| 29.3 | 5 |
| 29.6 | 4 |
| 29.9 | 4 |
| 30.9 | 5 |
| 31.0 | 4 |
| 33.6 | 7 |
| 34.1 | 7 |
| 35.0 | 12 |

Example 16

Preparation of Form J of Compound (I)

49.6 mg of Form B of compound (I) was dissolved in 2 mL of methyl isobutyl ketone at 22° C. The vial was opened and stored for five days to allow evaporation of the solvent at ambient condition, the resulting solid was obtained as Form J.

Figure 19:
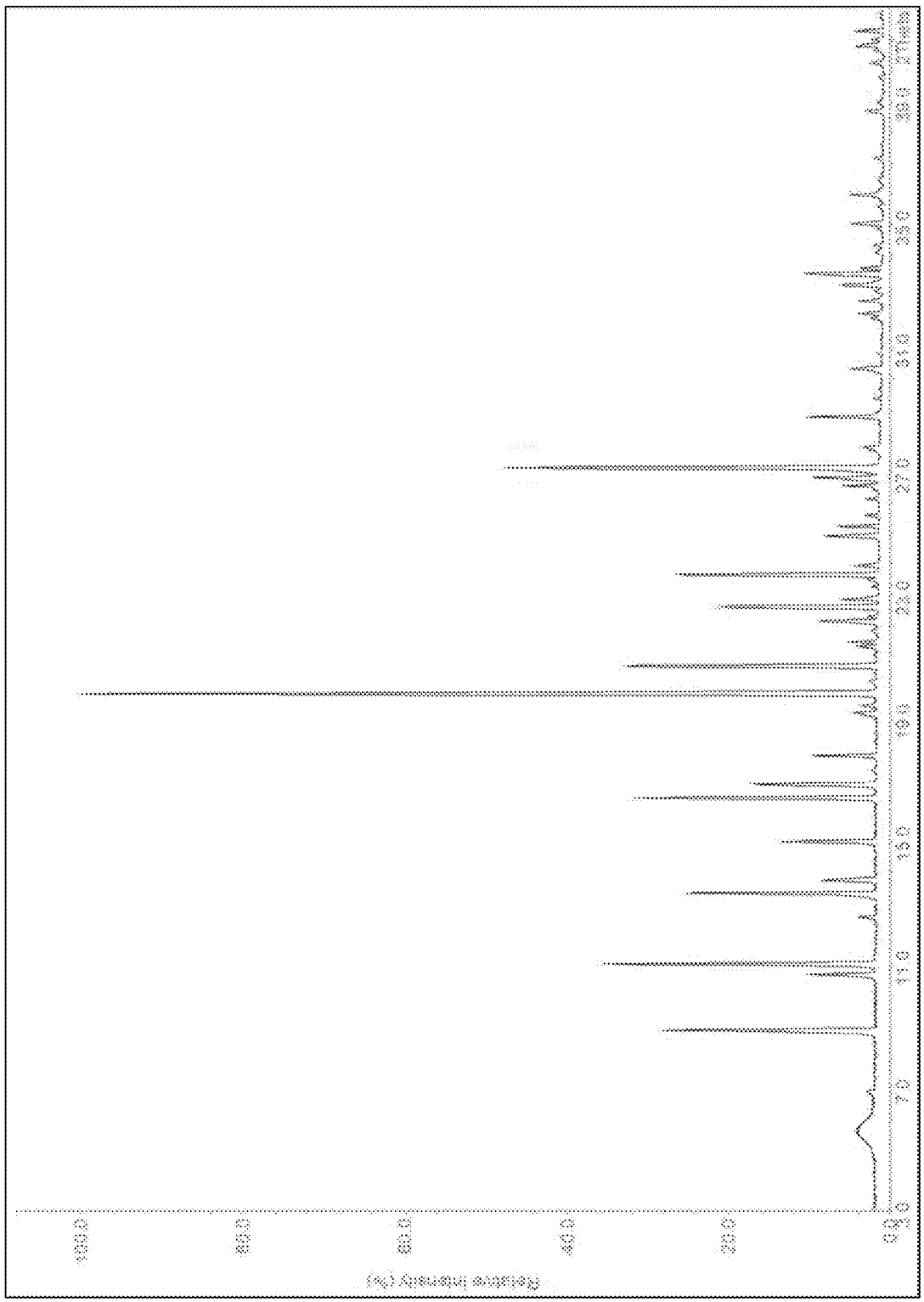

The XRPD pattern of Form J of compound (I) is shown in FIG. 19. Major peaks and their related intensities in the XRPD pattern are shown in Table 14. Form J is a methyl isobutyl ketone solvate of compound (I).

Characterization Method:

XRPD: X-ray diffraction patterns were recorded at ambient conditions in transmission geometry with a Stoe Stadi P diffractometer (Cu Kα1 radiation (1.5406 Å), 40 kV and 40 mA, primary beam monochromator, silicon strip detector, angular range 3° to 42° 2-theta with a step size of 0.02° 2-theta, approximately 30 minutes total measurement time). The samples were prepared and analyzed without further processing (e.g. grinding or sieving) of the substance.

TABLE 14

X-Ray Powder Diffraction peaks of Form J of compound (I).

| Pos. [°2-theta] | Rel. Int. [%] |
|---|---|
| 8.9 | 25 |
| 10.7 | 8 |
| 11.0 | 28 |
| 13.3 | 24 |
| 13.7 | 7 |
| 15.0 | 11 |
| 16.4 | 29 |
| 16.9 | 15 |
| 17.8 | 7 |
| 19.8 | 100 |
| 20.7 | 31 |
| 22.1 | 7 |
| 22.6 | 20 |
| 22.8 | 5 |
| 23.7 | 25 |
| 23.9 | 3 |
| 24.9 | 7 |
| 25.2 | 5 |
| 26.6 | 4 |
| 26.8 | 8 |
| 27.1 | 47 |
| 28.8 | 9 |
| 30.3 | 4 |
| 33.1 | 5 |
| 33.4 | 10 |
| 35.1 | 4 |
| 36.0 | 4 |

Example 17

Stability of Solid Forms 40 mg compound (I) in different solid forms were stored in a stability chamber with temperature and humidity controlled at 40° C. and 75%-RH, respectively. After 1 month, the samples were analyzed by XRPD to check their solid form and compared with their initial solid form. According to the results shown in Table 15. Form A, B, C, and G showed better stability than the original amorphous form as prepared in Example 1.

TABLE 15

Physical stability data of different solid forms of compound (I)

| | Physical stability | |
|---|---|---|
| Samples | Initial | 40° C./75%-RH, 1 month |
| Example 1, Form Amorphous of compound (I) | Form Amorphous | solid form change |
| Example 10, Form A of compound (I) | Form A | no solid form change |
| Example 11, Form B of compound (I) | Form B | no solid form change |
| Example 2, Form C of compound (I) | Form C | no solid form change |
| Example 12, Form G of compound (I) | Form G | no solid form change |

Example 18

Apparent Solubility Study

Apparent solubility was determined by suspending 5 mg of compound (I) in different bio-relevant media including pH buffers, SGF, FaSSIF, and FeSSIF. The suspensions were equilibrated at 25° C. for 24 hours. The suspensions were then filtered through a 0.22 pin PVDF filter into a 2-mL HPLC vial. The quantitation of the filtrate was conducted by HPLC with reference to a standard solution. The solubility results of selected novel solid forms in this invention are shown in Table 16. Surprisingly the novel solid forms of this invention showed comparable apparent solubility to Form Amorphous.

TABLE 16

Apparent solubility of different solid forms

| | Sample | | | | | | | | | |
|---|---|---|---|---|---|---|---|---|---|---|
| | Example 1, Form Amorphous of compound (I) | | Example 2, Form C of compound (I) | | Example 10, Form A of compound (I) | | Example 11, Form B of compound (I) | | Example 12, Form G of compound (I) | |
| PH | Solubility (mg/mL) | Final pH | Solubility (mg/mL) | Final pH | Solubility (mg/mL) | Final pH | Solubility (mg/mL) | Final pH | Solubility (mg/mL) | Final pH |
| pH1 | >10 | 1.1 | >10 | 0.9 | >16.28 | 1.2 | >10 | 1.0 | >10 | 1.0 |
| pH3 | 9.57 | 3.5 | 4.98 | 3.1 | 12.87 | 3.4 | 6.92 | 2.98 | 6.44 | 3.2 |
| pH5 | 3.83 | 5.2 | 2.24 | 4.9 | 6.39 | 5.0 | 3.35 | 4.73 | 3.75 | 5.1 |
| pH7 | 4.05 | 7.1 | 2.19 | 6.7 | 6.24 | 7.2 | 3.40 | 6.83 | 3.70 | 7.0 |
| pH9 | 5.03 | 9.1 | 2.32 | 8.8 | 6.38 | 8.9 | 3.55 | 8.86 | 3.64 | 8.9 |
| SGF | >10 | 1.3 | >10 | 1.1 | >16.36 | 1.5 | >10 | 1.44 | >10 | 1.2 |
| FaSSIF | 6.93 | 6.6 | 2.19 | 6.5 | 6.33 | 6.7 | 3.82 | 6.43 | 2.49 | 6.4 |
| FeSSIF | 7.35 | 5.2 | 2.78 | 4.9 | 7.93 | 5.0 | 4.13 | 4.93 | 2.79 | 5.1 |

Example 19

Single Dose PK (SDPK) Study

Five male Wistar Han rats were administered a single oral dose of 100 or 200 mg/kg of compound (I) (either Form A or Form C). Drug was administered as a suspension in 2% klucel, 0.1% polysorbate 80 and 0.1% parabens in water. Samples were taken at various times up to 24 h and plasma was analysed for compound (I) (double prodrug), compound (Ia) (single prodrug) and compound (Ib) (single prodrug) and compound (III) (active Form).

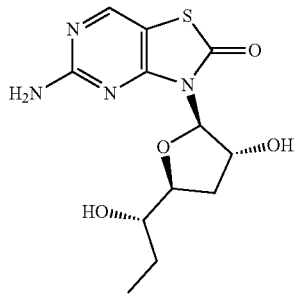

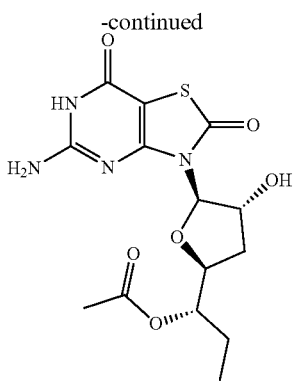

-continued

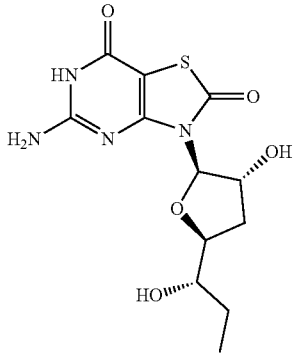

compound (Ia)(single prodrug); compound (Ib) (single prodrug); compound (III) (active form)

TABLE 17

| SDPK study of Form A and Form C of compound (I) in Wistar Han Rat (n = 5) | | | | |
|---|---|---|---|---|
| Parameter | Compound (I) | Compound (Ia) | Compound (Ib) | Compound (III) |
| PO 100 mg/kg of Example 10, Form A of compound (I) | | | | |
| $T_{max}$ (h) | 1.5 | 0.5 | 0.25 | 0.5 |
| $C_{max}$ (ng/mL) | 563 | 24767 | 231 | 7103 |
| PO 200 mg/kg of Example 4, Form C of compound (I) | | | | |
| $T_{max}$ (h) | 0.33 | 0.67 | 0.42 | 0.5 |
| $C_{max}$ (ng/mL) | 259 | 23233 | 258 | 5900 |

Compared with Form C of compound (I) dosing at 200 mg/kg, Form A of compound (I) dosing at 100 mg/kg exhibits faster conversion rate with shorter $T_{max}$ and higher $C_{max}$ for single prodrug (Ia) (0.5 h vs 0.67 h; 24767 ng/mL vs 23233 ng/mL), and higher $C_{max}$ of active form (7103 ng/mL vs 5900 ng/mL) in vivo study. Surprisingly Form A shows comparable or better SDPK profile than Form C even at half dose of the later, therefore Form A of compound (I) whose efficacy is driven by $C_{max}$ is more suitable to be formulated as immediate-release oral formulation.

The foregoing description is intended to illustrate various aspects of the instant invention. It is not intended that the examples presented herein limit the scope of the appended claims. The invention now being fully described, it will be apparent to one of ordinary skill in the art that many changes and modifications can be made thereto without departing from the spirit or scope of the appended claims.

The invention claimed is:

1. A solid form of compound (I),

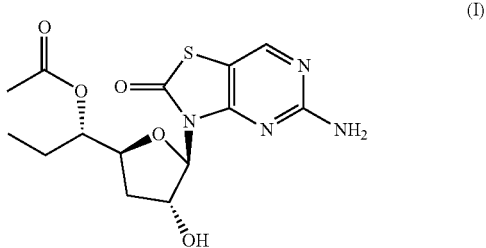 [SMILES: CC[C@H](OC(C)=O)[C@@H]1C[C@@H](O)[C@H](n2c(=O)sc3cnc(N)nc32)O1]

or a salt, or a solvate thereof, wherein the form is Form H, Form I, or Form J, or a combination thereof.

2. A solid form according to claim 1, wherein the solid form is Form H that exhibits an X-ray powder diffraction (XRPD) pattern with characteristic peaks expressed in degrees 2-theta at 11.4°±0.2°, 15.6°±0.2°, 17.3°±0.2°, 21.1°±0.2° and 21.9°±0.2°.

3. A solid form according to claim 2, wherein the solid form is Form H that exhibits an X-ray powder diffraction (XRPD) pattern with characteristic peaks expressed in degrees 2-theta at 6.7°±0.2°, 9.4°±0.2°, 11.1°±0.2°, 11.4°±0.2°, 15.6°±0.2°, 17.3°±0.2°, 17.6°±0.2°, 18.9°±0.2°, 19.5°±0.2°, 21.1°±0.2°, 21.9°±0.2°, 23.2°±0.2°, 25.8°±0.2° and 29.0°±0.2°.

4. A solid form according to claim 2, wherein the solid form is Form H that exhibits an X-ray powder diffraction (XRPD) pattern shown in FIG. 17.

5. A solid form according to claim 2, wherein the Form H is a dimethyl carbonate solvate of compound (I).

6. A solid form according to claim 1, wherein the solid form is Form I that exhibits an X-ray powder diffraction (XRPD) pattern with characteristic peaks expressed in degrees 2-theta at 11.1°±0.2°, 15.4°±0.2°, 17.2°±0.2°, 17.6°±0.2°, 20.9°±0.2° and 21.7°±0.2°.

7. A solid form according to claim 6, wherein the solid form is Form I that exhibits an X-ray powder diffraction (XRPD) pattern with characteristic peaks expressed in degrees 2-theta at 9.4°±0.2°, 11.1°±0.2°, 13.8°±0.2°, 14.2°±0.2°, 15.4°±0.2°, 17.2°±0.2°, 17.6°±0.2°, 19.2°±0.2°, 20.9°±0.2°, 21.7°±0.2°, 22.0°±0.2°, 23.0°±0.2°, 24.0°±0.2°, 25.2°±0.2° and 28.9°±0.2°.

8. A solid form according to claim 6, wherein the solid form is Form I that exhibits an X-ray powder diffraction (XRPD) pattern shown in FIG. 18.

9. A solid form according to claim 6, wherein the Form I is a methyl ethyl ketone solvate of compound (I).

10. A solid form according to claim 1, wherein the solid form is Form J that exhibits an X-ray powder diffraction (XRPD) pattern with characteristic peaks expressed in degrees 2-theta at 8.9°±0.2°, 11.0°±0.2°, 16.4°±0.2°, 19.8°±0.2°, 20.7°±0.2°, 23.7°±0.2° and 27.1°±0.2°.

11. A solid form according to claim 10, wherein the solid form is Form J that exhibits an X-ray powder diffraction (XRPD) pattern with characteristic peaks expressed in degrees 2-theta at 8.9°±0.2°, 11.0°±0.2°, 13.3°±0.2°, 15.0°±0.2°, 16.4°±0.2°, 16.9°±0.2°, 19.8°±0.2°, 20.7°±0.2°, 22.6°±0.2°, 23.7°±0.2°, 27.1°±0.2° and 33.4°±0.2°.

12. A solid form according to claim 10, wherein the solid form is Form J that exhibits an X-ray powder diffraction (XRPD) pattern shown in FIG. 19.

13. A solid form according to claim 10, wherein the Form J is a methyl isobutyl ketone solvate of compound (I).

14. A pharmaceutical composition comprising the solid form of claim 1 and a pharmaceutically acceptable carrier, excipient, diluent, adjuvant, vehicle or a combination thereof.

15. A method for the treatment of HBV infection or a disease caused by HBV infection, which method comprises administering a therapeutically effective amount of the solid form as defined in claim 1 to a subject in need thereof.

16. A method for the treatment of HBV infection or a disease caused by HBV infection, which method comprises administering a pharmaceutical composition of claim 14 to a subject in need thereof.

* * * * *